(12) United States Patent
Funke et al.

(10) Patent No.: US 8,299,036 B2
(45) Date of Patent: Oct. 30, 2012

(54) ACTIVE AGENT COMBINATIONS WITH INSECTICIDAL AND ACARICIDAL PROPERTIES

(75) Inventors: Christian Funke, Leichlingen (DE); Thomas Bretschneider, Lohmar (DE); Reiner Fischer, Monheim am Rhein (DE); Rüdiger Fischer, Pulheim (DE); Heike Hungenberg, Lagenfeld (DE); Wolfram Andersch, Bergisch Gladbach (DE); Wolfgang Thielert, Odenthal (DE); Anton Kraus, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 1290 days.

(21) Appl. No.: 10/578,512

(22) PCT Filed: Oct. 10, 2004

(86) PCT No.: PCT/EP2004/012329
§ 371 (c)(1), (2), (4) Date: Apr. 5, 2007

(87) PCT Pub. No.: WO2005/048712
PCT Pub. Date: Jun. 2, 2005

(65) Prior Publication Data
US 2008/0027114 A1    Jan. 31, 2008

(30) Foreign Application Priority Data
Nov. 14, 2003 (DE) .................................. 103 53 281

(51) Int. Cl.
*A01N 43/22* (2006.01)
*A01N 43/40* (2006.01)
*A01N 43/90* (2006.01)
*A01P 7/04* (2006.01)

(52) U.S. Cl. ........................... 514/30; 514/28; 514/341

(58) Field of Classification Search ................ 514/341, 514/462, 28, 30
See application file for complete search history.

(56) References Cited

U.S. PATENT DOCUMENTS

| | | | |
|---|---|---|---|
| 3,264,177 A | 8/1966 | Kenaga | |
| 4,962,126 A | 10/1990 | Drabek | |
| 5,262,383 A * | 11/1993 | Fischer | 504/195 |
| 5,478,855 A | 12/1995 | Suzuki et al. | |
| 5,610,122 A | 3/1997 | Fischer et al. | |
| 5,830,825 A | 11/1998 | Fischer et al. | |
| 5,945,444 A | 8/1999 | Fischer et al. | |
| 5,994,274 A | 11/1999 | Fischer et al. | |
| 6,051,723 A | 4/2000 | Fischer et al. | |
| 6,110,872 A | 8/2000 | Lieb et al. | |
| 6,114,374 A | 9/2000 | Lieb et al. | |
| 6,140,358 A | 10/2000 | Lieb et al. | |
| 6,251,830 B1 | 6/2001 | Fischer et al. | |
| 6,255,342 B1 | 7/2001 | Lieb et al. | |
| 6,288,102 B1 | 9/2001 | Hagemann et al. | |
| 6,316,486 B1 | 11/2001 | Lieb et al. | |
| 6,358,887 B1 | 3/2002 | Fischer et al. | |
| 6,417,370 B1 | 7/2002 | Lieb et al. | |
| 6,451,843 B1 | 9/2002 | Lieb et al. | |
| 6,458,965 B1 | 10/2002 | Lieb et al. | |
| 6,511,942 B1 | 1/2003 | Lieb et al. | |
| 6,589,976 B1 | 7/2003 | Fischer et al. | |
| 6,706,758 B2 | 3/2004 | Fischer et al. | |
| 6,762,183 B2 | 7/2004 | Fischer et al. | |
| 6,861,391 B1 | 3/2005 | Fischer et al. | |
| 6,893,651 B1 | 5/2005 | Fischer et al. | |
| 6,900,190 B2 | 5/2005 | Fischer et al. | |
| 6,933,261 B2 | 8/2005 | Lieb et al. | |
| 7,199,138 B2 | 4/2007 | Finkelstein et al. | |
| 7,256,158 B2 | 8/2007 | Lieb et al. | |
| 7,361,653 B2 | 4/2008 | Sakata et al. | |
| 7,585,887 B2 | 9/2009 | Fischer et al. | |
| 7,718,706 B2 | 5/2010 | Lieb et al. | |
| 7,902,231 B2 * | 3/2011 | Lahm et al. | 514/341 |
| 2003/0216260 A1 | 11/2003 | Ruther et al. | |
| 2004/0198987 A1 | 10/2004 | Freudenberger et al. | |
| 2007/0142327 A1 | 6/2007 | Funke et al. | |
| 2007/0232598 A1 | 10/2007 | Funke et al. | |
| 2007/0259787 A1 | 11/2007 | Ohkawara | |
| 2007/0270416 A1 | 11/2007 | Funke et al. | |
| 2008/0027046 A1 * | 1/2008 | Annan et al. | 514/229.2 |
| 2008/0070863 A1 | 3/2008 | Funke et al. | |
| 2010/0168042 A1 | 7/2010 | Funke et al. | |
| 2010/0249070 A1 | 9/2010 | Funke et al. | |
| 2010/0256195 A1 | 10/2010 | Fischer et al. | |
| 2010/0292226 A1 | 11/2010 | Funke et al. | |

FOREIGN PATENT DOCUMENTS

| | | |
|---|---|---|
| EP | 0 210 487 A1 | 2/1987 |
| EP | 0 234 045 A2 | 9/1987 |
| EP | 0 347 488 B1 | 12/1989 |
| EP | 0 528 156 A1 | 2/1993 |
| EP | 0 647 637 A1 | 4/1995 |
| WO | WO 93/10083 | 5/1993 |
| WO | WO 93/22297 | 11/1993 |
| WO | WO 95/26345 | 10/1995 |
| WO | WO 96/20196 | 7/1996 |

(Continued)

OTHER PUBLICATIONS

U.S. Appl. No. 10/581,348, inventors Funke et al., filed Jun. 2, 2006.
Dialog File 351, Accession No. 3940248, Derwent WPI English language abstract for EP 0 210 487 (listed on accompanying PTO/SB/08A as document FP1).
Dialog File 351, Accession No. 6602040, Derwent WPI English language abstract for EP 0 528 156 (listed on accompanying PTO/SB/08A as document FP4).
Dialog File 351, Accession No. 7358770, Derwent WPI English language abstract for EP 0 647 637 (listed on accompanying PTO/SB/08A as document FP7).
Bauer, T.A., et al., "Response of Selected Weed Species to Postemergence Imazethapyr and Bentazon," *Weed Tech.* 9:236-242, The Weed Science Society of America (1995).

(Continued)

*Primary Examiner* — John Pak
(74) *Attorney, Agent, or Firm* — Sterne, Kessler, Goldstein & Fox P.L.L.C.

(57) ABSTRACT

The invention relates to novel insecticidal active compound combinations comprising, firstly, cyclic ketoenols or other acaricidally active compounds and, secondly, further insecticidally active compounds from the group of the anthranilamides, which combinations are highly suitable for controlling animal pests, such as insects and unwanted acarids.

3 Claims, No Drawings

FOREIGN PATENT DOCUMENTS

| | | |
|---|---|---|
| WO | WO 96/25395 | 8/1996 |
| WO | WO 96/35664 | 11/1996 |
| WO | WO 97/01535 | 1/1997 |
| WO | WO 97/02243 | 1/1997 |
| WO | WO 97/36868 | 10/1997 |
| WO | WO 98/05638 | 2/1998 |
| WO | WO 98/25928 | 6/1998 |
| WO | WO 99/16748 | 4/1999 |
| WO | WO 99/43649 | 9/1999 |
| WO | WO 99/48869 | 9/1999 |
| WO | WO 99/55673 | 11/1999 |
| WO | WO 01/23354 A2 | 4/2001 |
| WO | WO 01/24634 A1 | 4/2001 |
| WO | WO 01/74770 A1 | 10/2001 |
| WO | WO 01/76369 A2 | 10/2001 |
| WO | WO 02/37963 A1 | 5/2002 |
| WO | WO 02/087334 A1 | 11/2002 |
| WO | WO 03-015518 * | 2/2003 |
| WO | WO 03/015519 A1 | 2/2003 |
| WO | WO 03/016284 A1 | 2/2003 |
| WO | WO 2005/079575 A1 | 9/2005 |
| WO | WO 2005/107468 A1 | 11/2005 |
| WO | WO 2006/007595 A2 | 1/2006 |
| WO | WO 2006/108552 A2 | 10/2006 |

OTHER PUBLICATIONS

Blackshaw, R.E., "HOE-39866 Use in Chemical Fallow Systems," Weed Tech. 3:420-428, The Weed Science Society of America (1989).

Blackshaw, R.E., "Synergistic Mixes of DPX-A7881 and Clopyralid in Canola (Brassica napus)," Weed Tech. 3:690-695, The Weed Science Society of America (1989).

Blackshaw, R.E., et al., "Herbicide Combinations for Postemergent Weed Control in Safflower (Carthamus tinctorius)," Weed Tech. 4:97-104, The Weed Science Society of America (1990).

Blouin, D.C., et al., "Analysis of Synergistic and Antagonistic Effects of Herbicides Using Nonlinear Mixed-Model Methodology," Weed Tech. 18:464-472, The Weed Science Society of America (2004).

Bradley, P.R., et al., "Response of Sorghum (Sorghum bicolor) to Atrazine, Ammonium Sulfate, and Glyphosate," Weed Tech. 14:15-18, The Weed Science Society of America (2000).

Buker, III, R.S., et al., "Confirmation and Control of a Paraquat-Tolerant Goosegrass (Eleusine indica) Biotype," Weed Tech. 16:309-313, The Weed Science Society of America (2002).

Burke, I.C., et al., "CGA-362622 Antagonizes Annual Grass Control with Clethodim," Weed Tech. 16:749-754, The Weed Science Society of America (2002).

Colby, S.R., "Calculating Synergistic and Antagonistic Responses of Herbicide Combinations," Weeds 15:20-22, Weed Society of America (1967).

Flint, J.L., et al., "Analyzing Herbicide Interactions, A Statistical Treatment of Colby's Method," Weed Tech. 2:304-309, The Weed Science Society of America (1988).

Gillespie, G-R., and Nalewaja, J.D., "Wheat (Triticum aestivum) Response to Triallate Plus Chlorsulfuron," Weed Tech. 3:20-23, The Weed Science Society of America (1989).

Green, J.M., et al., "Metribuzin and Chlorimuron Mixtures for Preemergence Broadleaf Weed Control in Soybeans, Glycine max," Weed Tech. 2:355-363, The Weed Science Society of America (1988).

Harker, N.K., and O'Sullivan, P.A., "Synergistic Mixtures of Sethoxydim and Fluazifop on Annual Grass Weeds," Weed Tech. 5:310-316, The Weed Science Society of America (1991).

Kent, L.M., et al., "Effect of Ammonium Sulfate, Imazapyr, and Environment on the Phytotoxicity of Imazethapyr," Weed Tech. 5:202-205, The Weed Science Society of America (1991).

Kotoula-Syka, E., et al., "Interactions between SAN 582H and Selected Safeners on Grain Sorghum (Sorghum bicolor) and Corn (Zea mays)," Weed Tech. 10:299-304, The Weed Science Society of America (1996).

Lanclos, D.Y., et al., "Glufosinate Tank-Mix Combinations in Glufosinate-Resistant Rice (Oryza sativa)," Weed Tech. 16:659-663, The Weed Science Society of America (2002).

Norris, J.L., et al., "Weed Control from Herbicide Combinations with Three Formulations of Glyphosate," Weed Tech. 15:552-558, The Weed Science Society of America (2001).

Novosel, K.M., et al., "Metolachlor Efficacy as Influenced by Three Acetolactate Synthase-Inhibiting Herbicides," Weed Tech. 12:248-253, The Weed Science Society of America (1998).

Palmer, E.W., et al., "Broadleaf Weed Control in Soybean (Glycine max) with CGA-277476 and Four Postemergence Herbicides," Weed Tech. 14:617-623, The Weed Science Society of America (2000).

Rummens, F.H.A., "An Improved Definition of Synergistic and Antagonistic Effects," Weed Science 23(1):4-6, The Weed Science Society of America, United States (1975).

Salzman, F.P., and Renner, K.A., "Response of Soybean Combinations of Clomazone, Metribuzin, Linuron, Alachlor, and Atrazine," Weed Tech. 6:922-929, The Weed Science Society of America (1992).

Scott, R.C., et al., "Spray Adjuvant, Formulation, and Environmental Effects of Synergism from Post-Applied Tank Mixtures of SAN 582H with Fluazifop-P, Imazethapyr, and Sethoxydim," Weed Tech. 12:463-469, The Weed Science Society of America (1998).

Shaw, D.R. and Arnold, J.C., "Weed Control from Herbicide Combinations with Glyphosate," Weed Tech. 16:1-6, The Weed Science Society of America (2002).

Snipes, C.E., and Allen, R.L., "Interaction of Graminicides Applied in Combination with Pyrithiobac," Weed Tech. 10:889-892, The Weed Science Society of America (1996).

Sun, Y.-P. & Johnson, E.R., "Analysis of Joint Action of Insecticides against House Flies", J. Econ. Entomol., 53:887-892, Journal of Economic Entomology, United States (1960).

Wehtje, G. and Walker, R.H., "Interaction of Glyphosate and 2,4-DB for the Control of Selected Morningglory (Ipomoea spp.) Species," Weed Tech. 11:152-156, The Weed Science Society of America (1997).

Zhang, W., et al., "Fenoxaprop Interactions for Barnyardgrass (Echinochloa crus-galli) Control in Rice," Weed Tech. 19:293-297, The Weed Science Society of America (2005).

Office Action mailed Feb. 16, 1993, in U.S. Appl. No. 07/909,939, Fischer et al., filed Jul. 7, 1992.

Office Action mailed May 3, 2004, in U.S. Appl. No. 10/239,332, Fischer et al., filed Sep. 20, 2002.

Office Action mailed Oct. 29, 2004, in U.S. Appl. No. 10/239,332, Fischer et al., filed Sep. 20, 2002.

Office Action mailed Nov. 14, 2003, in U.S. Appl. No. 10/221,970, Fischer et al., filed Sep. 16, 2002.

Tomlin, C.D.S., ed., "Index 5," in The Pesticide Manual, Twelfth Edition, p. 1243-1250, The British Crop Protection Council, United Kingdom (2000).

\* cited by examiner

ACTIVE AGENT COMBINATIONS WITH INSECTICIDAL AND ACARICIDAL PROPERTIES

This application is a 35 U.S.C. §371 U.S. National Phase filing of International Application No. PCT/EP2004/012329, filed Oct. 30, 2004, which claims the benefit of German Patent Application No. 103 53 281.1, filed Nov. 14, 2003.

The invention relates to novel active compound combinations comprising, firstly, known cyclic ketoenols and, secondly, further known insecticidally active compounds, which combinations are highly suitable for controlling animal pests, such as insects and unwanted acarids.

It is already known that certain cyclic ketoenols have fungicidal, insecticidal and acaricidal properties (EP-A 0 528 156, EP-A 0 647 637, WO 95/26 345, WO 96/20196, WO 96/25395, WO 96/35664, WO 97/01535, WO 97/02243, WO 97/36868, WO 98/05638, WO 98/25928, WO 99/16748, WO 99/43649, WO 99/48869, WO 99/55673, WO 01/23354 and WO 01/74770). The activity of these compounds is good; however, at low application rates it is sometimes unsatisfactory.

It is also known that mixtures of phthalamides and other bioactive compounds have insecticidal and/or acaricidal action (WO 02/087334). The action of these mixtures is not always optimal.

Furthermore, it is already known that numerous heterocycles, organotin compounds, benzoylureas and pyrethroids have insecticidal and acaricidal properties (cf. WO 93/22297, WO 93/10083, DE-A 26 41 343, EP-A 0 347 488, EP-A 0 210 487, U.S. Pat. No. 3,264,177 and EP-A 0 234 045). However, the action of these compounds is not always satisfactory.

It has now been found that active compound combinations comprising compounds of the formula (I) (group 1)

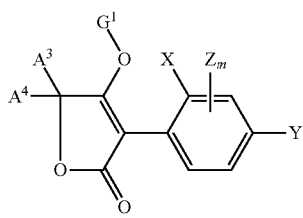

in which
X represents $C_1$-$C_6$-alkyl, bromine, $C_1$-$C_6$-alkoxy or $C_1$-$C_3$-haloalkyl,
Y represents hydrogen, $C_1$-$C_6$-alkyl, halogen, $C_1$-$C_6$-alkoxy, $C_1$-$C_3$-haloalkyl,
Z represents $C_1$-$C_6$-alkyl, halogen, $C_1$-$C_6$-alkoxy,
m represents a number 0-3,
$A^3$ represents hydrogen or in each case optionally halogen-substituted straight-chain or branched $C_1$-$C_{12}$-alkyl, $C_2$-$C_8$-alkenyl, $C_2$-$C_8$-alkynyl, $C_1$-$C_{10}$-alkoxy-$C_1$-$C_8$-alkyl, $C_1$-$C_8$-polyalkoxy-$C_2$-$C_8$-alkyl, $C_1$-$C_{10}$-alkylthio-$C_2$-$C_8$-alkyl, cycloalkyl having 3-8 ring atoms which may be interrupted by oxygen and/or sulfur or in each case optionally halogen-, $C_1$-$C_6$-alkyl-, $C_1$-$C_6$-haloalkyl-, $C_1$-$C_6$-alkoxy-, $C_1$-$C_6$-haloalkoxy, nitro-substituted phenyl or phenyl-$C_1$-$C_6$-alkyl,
$A^4$ represents hydrogen, $C_1$-$C_6$-alkyl or $C_1$-$C_6$-alkoxy-$C_1$-$C_4$-alkyl
or in which
$A^3$ and $A^4$ together with the carbon atom to which they are attached form a saturated or unsaturated 3- to 8-membered ring which is optionally interrupted by oxygen and/or sulfur and optionally substituted by halogen, $C_1$-$C_6$-alkyl, $C_1$-$C_6$-alkoxy, $C_1$-$C_4$-haloalkyl, $C_1$-$C_4$-haloalkoxy, $C_1$-$C_4$-alkylthio or optionally substituted phenyl or is optionally benzo-fused,
$G^1$ represents hydrogen (a) or represents the groups

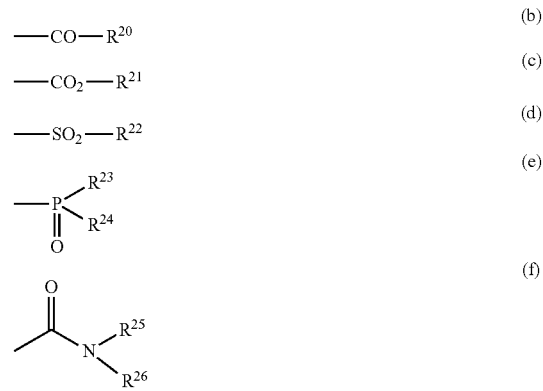

in which
$R^{20}$ represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, $C_1$-$C_8$-polyalkoxy-$C_2$-$C_8$-alkyl or cycloalkyl having 3-8 ring atoms which may be interrupted by oxygen and/or sulfur atoms,
represents optionally halogen-, nitro-, $C_1$-$C_6$-alkyl-, $C_1$-$C_6$-alkoxy-, $C_1$-$C_6$-haloalkyl-, $C_1$-$C_6$-haloalkoxy-substituted phenyl;
represents optionally halogen-, $C_1$-$C_6$-alkyl-, $C_1$-$C_6$-alkoxy-, $C_1$-$C_6$-haloalkyl-, $C_1$-$C_6$-haloalkoxy-substituted phenyl-$C_1$-$C_6$-alkyl,
represents in each case optionally halogen- and/or $C_1$-$C_6$-alkyl-substituted pyridyl, pyrimidyl, thiazolyl or pyrazolyl, represents optionally halogen- and/or $C_1$-$C_6$-alkyl-substituted phenoxy-$C_1$-$C_6$-alkyl,
$R^{21}$ represents in each case optionally halogen-substituted $C_1$-$C_{20}$-alkyl, $C_2$-$C_{20}$-alkenyl, $C_1$-$C_8$-alkoxy-$C_2$-$C_8$-alkyl or $C_1$-$C_8$-polyalkoxy-$C_2$-$C_8$-alkyl,
represents in each case optionally halogen-, nitro-, $C_1$-$C_6$-alkyl-, $C_1$-$C_6$-alkoxy-, $C_1$-$C_6$-haloalkyl-substituted phenyl or benzyl,
$R^{22}$ represents optionally halogen-substituted $C_1$-$C_8$-alkyl, represents in each case optionally $C_1$-$C_4$-alkyl-, halogen-, $C_1$-$C_4$-haloalkyl-, $C_1$-$C_4$-alkoxy-, $C_1$-$C_4$-haloalkoxy-, nitro- or cyano-substituted phenyl or benzyl,
$R^{23}$ and $R^{24}$ independently of one another represent in each case optionally halogen-substituted $C_1$-$C_8$-alkyl, $C_1$-$C_8$-alkoxy, $C_1$-$C_8$-alkylamino, di($C_1$-$C_8$)alkylamino, $C_1$-$C_8$-alkylthio, $C_2$-$C_5$-alkenylthio, $C_2$-$C_5$-alkynylthio, $C_3$-$C_7$-cycloalkylthio, represent in each case optionally halogen-, nitro-, cyano-, $C_1$-$C_4$-alkoxy, $C_1$-$C_4$-haloalkoxy-, $C_1$-$C_4$-alkylthio-, $C_1$-$C_4$-haloalkylthio-, $C_1$-$C_4$-alkyl-, $C_1$-$C_4$-haloalkyl-substituted phenyl, phenoxy or phenylthio,
$R^{25}$ and $R^{26}$ independently of one another represent in each case optionally halogen-substituted $C_1$-$C_{10}$-alkyl, $C_1$-$C_{10}$-alkoxy, $C_3$-$C_8$-alkenyl, $C_1$-$C_8$-alkoxy-$C_1$-$C_8$-alkyl, represent optionally halogen-, $C_1$-$C_6$-haloalkyl-, $C_1$-$C_6$-alkyl- or $C_1$-$C_6$-alkoxy-substituted phenyl, represent optionally halogen-, $C_1$-$C_6$-alkyl-, $C_1$-$C_6$-haloalkyl- or $C_1$-$C_6$-alkoxy-substituted benzyl or together represent a 5- to 6-membered ring which is optionally interrupted by oxygen or sulfur and which may optionally be substituted by $C_1$-$C_6$-alkyl, or an acaricidally active compound (group 2), preferably (2-1) the phenylhyrazine derivative of the formula (known from WO 93/10083)

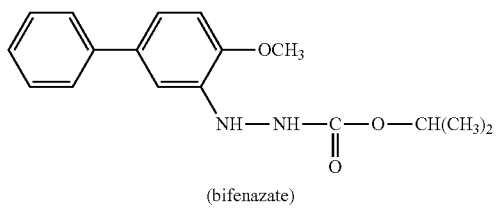

(bifenazate)

and/or (2-2) the macrolide with the common name abamectin (known from DE-A 27 17 040)

and/or (2-3) the naphthalenedione derivative of the formula (known from DE-A 26 41 343)

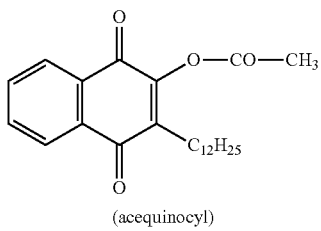

(acequinocyl)

and/or (2-4) the pyrrole derivative of the formula (known from EP-A 0 347 488)

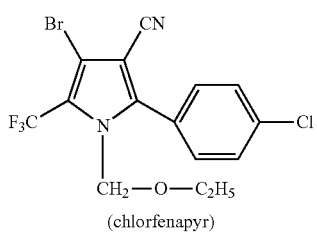

(chlorfenapyr)

and/or (2-5) the thiourea derivative of the formula (known from EP-A 0 210 487)

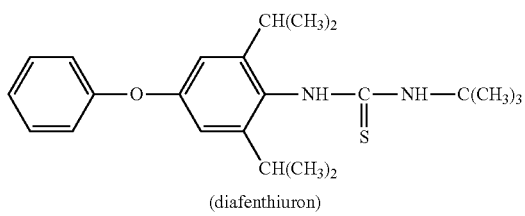

(diafenthiuron)

and/or (2-6) the oxazoline derivative of the formula (known from WO 93/22297)

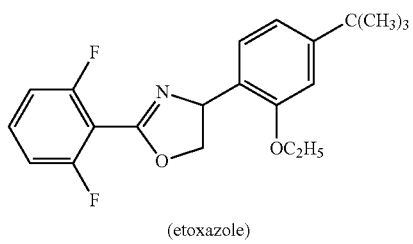

(etoxazole)

and/or (2-7) an organotin derivative of the formula

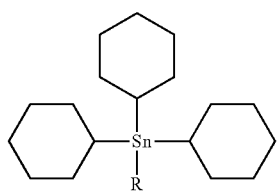

in which

R represents

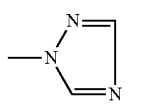

(2-7-a = azocyclotin), known from The Pesticide Manual, 9th edition, p. 48, or

R represents —OH (2-7-b=cyhexatin), known from U.S. Pat. No. 3,264,177 and/or (2-8) the pyrazole derivative of the formula (known from EP-A 0 289 879)

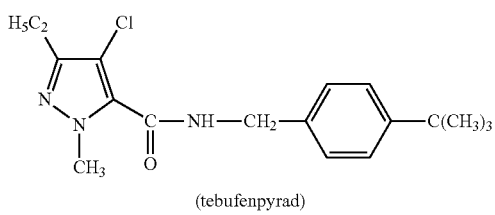

(tebufenpyrad)

and/or (2-9) the pyrazole derivative of the formula (known from EP-A 0 234 045)

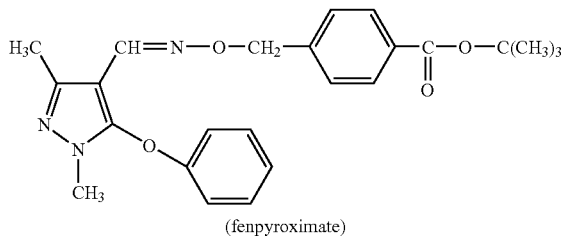

(fenpyroximate)

and/or (2-10) the pyridazinone derivative of the formula (known from EP-A 0 134 439)

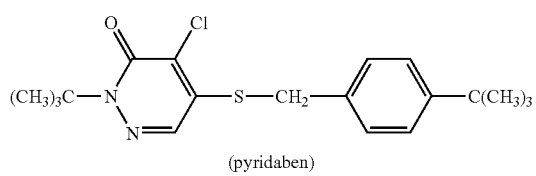

(pyridaben)

and/or (2-11) the benzoylurea derivative of the formula (known from EP-A 0 161 019)

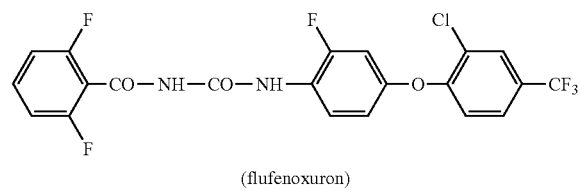

(flufenoxuron)

and/or (2-12) the pyrethroid of the formula (known from EP-A 0 049 977)

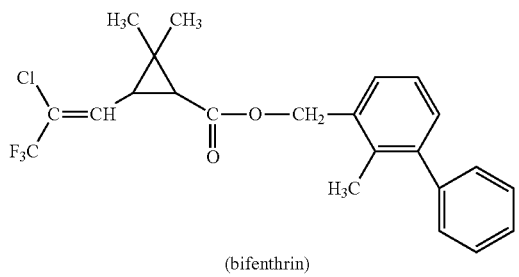

(bifenthrin)

and/or (2-13) the tetrazine derivative of the formula (known from EP-A 0 005 912)

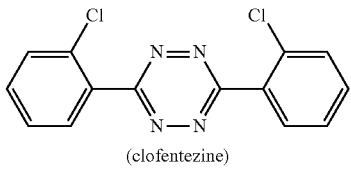

(clofentezine)

and/or (2-14) the organotin derivative of the formula (known from DE-A 21 15 666)

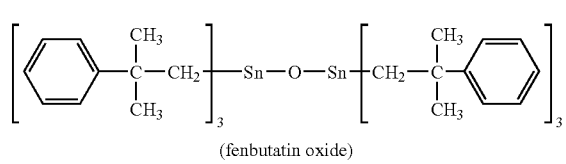

(fenbutatin oxide)

and/or (2-15) the sulfenamide of the formula (known from The Pesticide Manual, 11th edition, 1997, page 1208)

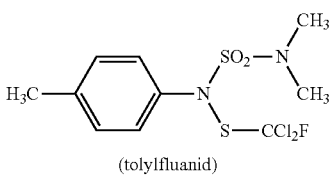

(tolylfluanid)

and/or (2-16) the pyrimidyl phenol ethers of the formula (known from WO 94/02470, EP-A 0 833 991)

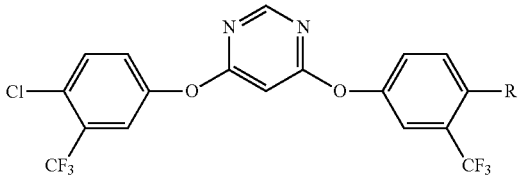

in which

R represents fluorine (2-16-a=4-[(4-chloro-α,α,α-trifluoro-3-tolyl)oxy]-6-[(α,α,α-4-tetrafluoro-3-tolyl)oxy]pyrimidine)

R represents nitro (2-16-b=4-[(4-chloro-α,α,α-trifluoro-3-tolyl)oxy]-6-[α,α,α-trifluoro-4-nitro-3-tolyl)oxy]pyrimidine)

R represents bromine (2-16-=4-[(4-chloro-α,α,α-trifluoro-3-tolyl)oxy]-6-[(α,α,α-trifluoro-4-bromo-3-tolyl)oxy]pyrimidine and/or (2-17) the macrolide of the formula (known from EP-A 0 375 316)

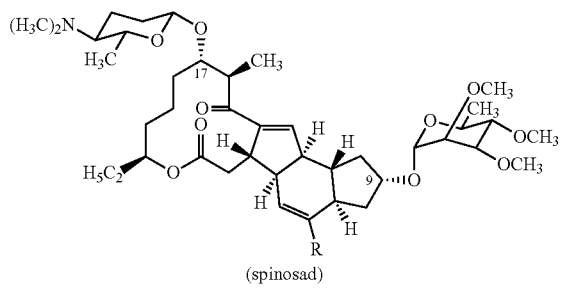

(spinosad)

a mixture comprising, preferably,
85% spinosyn A (R=H)
15% spinosyn B (R=CH$_3$)

and/or (2-18) ivermectin (known from EP-A 0 001 689)

and/or (2-19) milbemectin (known from The Pesticide Manual, 11th edition, 1997, p. 846)

and/or (2-20) endosulfan (known from DE-A 10 15 797)

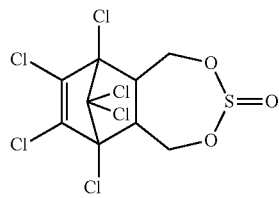

and/or (2-21) fenazaquin (known from EP-A 0 326 329)

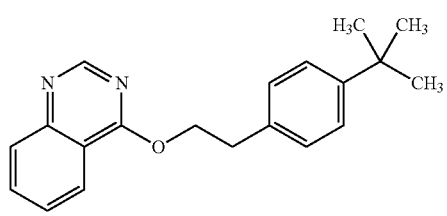

and/or (2-22) pyrimidifen (known from EP-A 0 196 524)

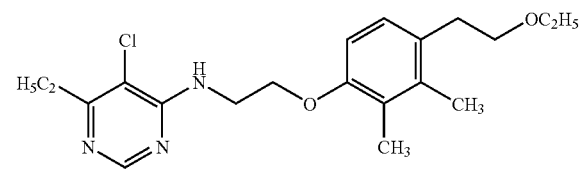

and/or (2-23) triarathen (known from DE-A 27 24 494)

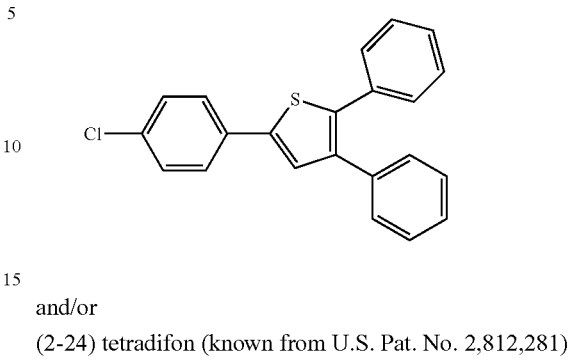

and/or (2-24) tetradifon (known from U.S. Pat. No. 2,812,281)

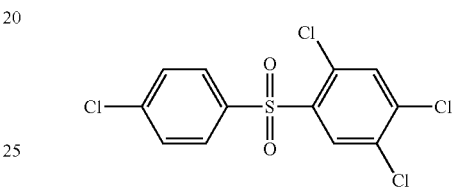

and/or (2-25) propargite (known from U.S. Pat. No. 3,272,854)

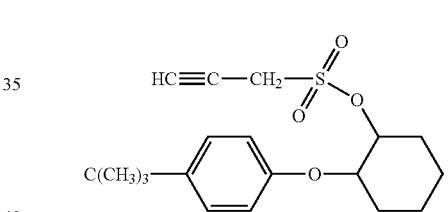

and/or (2-26) hexythiazox (known from DE-A 30 37 105)

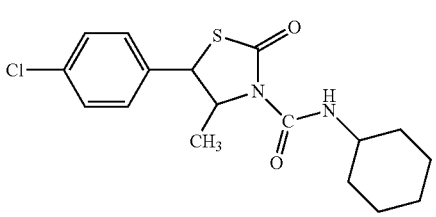

and/or (2-27) bromopropylate (known from U.S. Pat. No. 3,784,696)

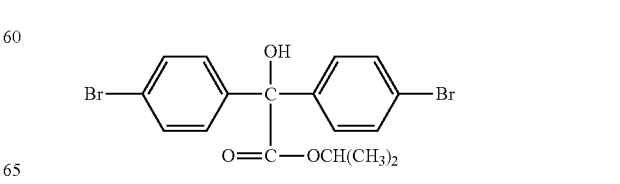

and/or
(2-28) dicofol (known from U.S. Pat. No. 2,812,280)

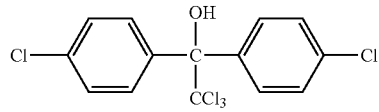

and/or
(2-29) chinomethionat (known from DE-A 11 00 372)

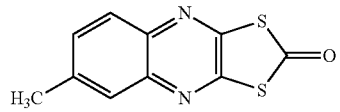

and at least one active compound from the group of the anthranilamides of the formula (II) are synergistically active and have very good insecticidal and acaricidal properties.

Surprisingly, the insecticidal and/or acaricidal action of the active compound combinations according to the invention is higher than the sum of the actions of the individual active compounds. Thus, an unforeseeable true synergistic effect is present, and not just an addition of actions.

In addition to at least one active compound of the formula (I) or an active compound of group 2 (compounds (2-1) to (2-29)), the active compound combinations according to the invention comprise at least one active compound of the formula (II).

Preference is given to active compound combinations comprising compounds of the formula (I) in which
X represents $C_1$-$C_4$-alkyl, bromine, $C_1$-$C_4$-alkoxy or $C_1$-$C_3$-haloalkyl,
Y represents hydrogen, $C_1$-$C_4$-alkyl, fluorine, chlorine, bromine, $C_1$-$C_4$-alkoxy, $C_1$-$C_3$-haloalkyl,
Z represents $C_1$-$C_4$-alkyl, chlorine, bromine, $C_1$-$C_4$-alkoxy,
m represents a number 0-2,
$A^3$ represents hydrogen or in each case optionally mono- to trifluoro-substituted straight-chain or branched $C_1$-$C_6$-alkyl, $C_2$-$C_6$-alkenyl, $C_1$-$C_4$-alkoxy-$C_1$-$C_2$-alkyl, cycloalkyl having 3-8 ring atoms which may optionally be interrupted by oxygen and/or sulfur or represents benzyl or phenyl which is optionally mono- to disubstituted by fluorine, chlorine, bromine, $C_1$-$C_2$-alkyl, $C_1$-$C_2$-haloalkyl, $C_1$-$C_2$-alkoxy, $C_1$-$C_2$-haloalkoxy, nitro,
$A^4$ represents hydrogen, $C_1$-$C_2$-alkyl or $C_1$-$C_2$-alkoxy-$C_1$-$C_2$-alkyl
or in which
$A^3$ and $A^4$ together with the carbon atom to which they are attached form a saturated or unsaturated 3- to 7-membered ring which is optionally interrupted by oxygen and/or sulfur and optionally mono- to disubstituted by fluorine, chlorine, $C_1$-$C_4$-alkyl, $C_1$-$C_4$-alkoxy, $C_1$-$C_2$-haloalkyl, $C_1$-$C_2$-haloalkoxy or $C_1$-$C_2$-alkylthio,
$G^1$ represents hydrogen (a) or represents groups (b) 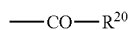

(c) 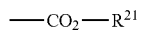

(d) 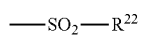

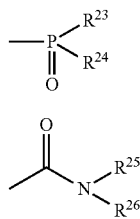

in which
$R^{20}$ represents in each case optionally mono- to pentafluoro- or -chloro-substituted $C_1$-$C_{16}$-alkyl, $C_2$-$C_{16}$-alkenyl, $C_1$-$C_4$-alkoxy-$C_1$-$C_4$-alkyl, $C_1$-$C_4$-alkylthio-$C_1$-$C_4$-alkyl or cycloalkyl having 3-6 ring atoms which may be interrupted by oxygen and/or sulfur atoms,
represents phenyl which is optionally mono- to disubstituted by fluorine, chlorine, bromine, nitro, $C_1$-$C_4$-alkyl, $C_1$-$C_4$-alkoxy, $C_1$-$C_4$-haloalkyl, $C_1$-$C_4$-haloalkoxy,
represents benzyl which is optionally mono to disubstituted by fluorine, chlorine, bromine, $C_1$-$C_4$-alkyl, $C_1$-$C_4$-alkoxy, $C_1$-$C_4$-haloalkyl, $C_1$-$C_4$-haloalkoxy,
represents pyridyl, pyrimidyl, thiazolyl or pyrazolyl, each of which is optionally mono- to disubstituted by chlorine, bromine and/or $C_1$-$C_4$-alkyl,
$R^{21}$ represents $C_1$-$C_{20}$-alkyl, $C_2$-$C_{20}$-alkenyl, $C_1$-$C_6$-alkoxy-$C_2$-$C_6$-alkyl, $C_1$-$C_6$-poly-alkoxy-$C_2$-$C_6$-alkyl, each of which is optionally mono- to pentasubstituted by fluorine or chlorine,
represents phenyl or benzyl, each of which is optionally mono- to disubstituted by fluorine, chlorine, bromine, nitro, $C_1$-$C_6$-alkyl, $C_1$-$C_6$-alkoxy, $C_1$-$C_4$-haloalkyl,
$R^{22}$ represents $C_1$-$C_4$-alkyl which is optionally mono- to pentasubstituted by fluorine or chlorine, represents phenyl or benzyl, each of which is optionally mono- to disubstituted by $C_1$-$C_4$-alkyl, fluorine, chlorine, bromine, $C_1$-$C_4$-haloalkyl, $C_1$-$C_4$-alkoxy, $C_1$-$C_4$-haloalkoxy, nitro or cyano,
$R^{23}$ and $R^{24}$ independently of one another represent $C_1$-$C_4$-alkyl, $C_1$-$C_4$-alkoxy, $C_1$-$C_4$-alkylamino, di($C_1$-$C_4$)alkylamino, $C_1$-$C_4$-alkylthio, $C_2$-$C_4$-alkenylthio, $C_3$-$C_6$-cycloalkylthio, each of which is optionally mono- to trisubstituted by fluorine or chlorine, represent phenyl, phenoxy or phenylthio, each of which is optionally mono- to disubstituted by fluorine, chlorine, bromine, nitro, cyano, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkyl, $C_1$-$C_2$-haloalkyl,
$R^{25}$ and $R^{26}$ independently of one another represent $C_1$-$C_6$-alkyl, $C_1$-$C_6$-alkoxy, $C_3$-$C_6$-alkenyl, $C_1$-$C_4$-alkoxy-$C_1$-$C_2$-alkyl, each of which is optionally mono- to trisubstituted by fluorine or chlorine, represent benzyl which is optionally mono- to disubstituted by fluorine, chlorine, bromine, $C_1$-$C_2$-haloalkyl, $C_1$-$C_4$-alkyl or $C_1$-$C_4$-alkoxy or together represent a 5- to 6-membered ring which is optionally interrupted by oxygen or sulfur and which may optionally be substituted by $C_1$-$C_2$-alkyl,
and at least one active compound of the formula (II).

In the radicals in the preferred ranges named halogen, halogen preferably represents chlorine and fluorine.

Particular preference is given to active compound combinations comprising compounds of the formula (I) in which
X represents $C_1$-$C_4$-alkyl, $C_1$-$C_4$-alkoxy or trifluoromethyl, Y represents hydrogen, $C_1$-$C_4$-alkyl, chlorine, bromine, $C_1$-$C_4$-alkoxy, $C_1$-$C_2$-haloalkyl, Z represents $C_1$-$C_4$-alkyl, chlorine, bromine, $C_1$-$C_4$-alkoxy, m represents 0 or 1, $A^3$ and $A^4$ together with the carbon atom to which they are attached represent a saturated 5- to 6-membered ring which is optionally monosubstituted by $C_1$-$C_4$-alkyl or $C_1$-$C_4$-alkoxy, $G^1$ represents hydrogen (a) or represents the groups —CO—$R^{20}$ (b)

—$CO_2$—$R^{21}$ (c), in which $R^{20}$ represents in each case optionally mono- to trifluoro- or -chloro-substituted $C_1$-$C_{12}$-alkyl, $C_2$-$C_{12}$-alkenyl, $C_1$-$C_4$-alkoxy-$C_1$-$C_2$-alkyl, or cycloalkyl having 3-6 ring atoms which may be interrupted by 1 to 2 oxygen atoms, represents phenyl which is optionally monosubstituted by fluorine, chlorine, bromine, nitro, $C_1$-$C_4$-alkyl, $C_1$-$C_4$-alkoxy, trifluoromethyl or trifluoromethoxy;

$R^{21}$ represents $C_1$-$C_{12}$-alkyl, $C_2$-$C_{12}$-alkenyl, $C_1$-$C_4$-alkoxy-$C_2$-$C_4$-alkyl, represents phenyl or benzyl, each of which is optionally monosubstituted by fluorine, chlorine, bromine, nitro, $C_1$-$C_4$-alkyl, $C_1$-$C_4$-alkoxy or trifluoromethyl, and at least one active compound of the formula (II).

Very particular preference is given to active compound combinations comprising compounds of the formula (I) in which X represents methyl, ethyl, methoxy, ethoxy or trifluoromethyl, Y represents hydrogen, methyl, ethyl, chlorine, bromine, methoxy or trifluoromethyl, Z represents methyl, ethyl, chlorine, bromine or methoxy, m represents 0 or 1, $A^3$ and $A^4$ together with the carbon atom to which they are attached form a saturated 5- to 6-membered ring which is optionally monosubstituted by methyl, ethyl, propyl, methoxy, ethoxy, propoxy, butoxy or isobutoxy, $G^1$ represents hydrogen (a) or represents the groups —CO—$R^{20}$ (b)

—$CO_2$—$R^{21}$ (c), in which $R^{20}$ represents in each case mono- to trifluoro- or -chloro-substituted $C_1$-$C_8$-alkyl, $C_2$-$C_8$-alkenyl, $C_1$-$C_3$-alkoxy-$C_1$-$C_2$-alkyl, or cycloalkyl having 3-6 ring atoms which may be interrupted by 1 to 2 oxygen atoms, represents phenyl which is optionally monosubstituted by fluorine, chlorine, bromine, methyl, methoxy, trifluoromethyl or trifluoromethoxy;

$R^{21}$ represents $C_1$-$C_8$-alkyl, $C_2$-$C_8$-alkenyl, $C_1$-$C_4$-alkoxy-$C_2$-$C_3$-alkyl, represents phenyl or benzyl, each of which is optionally monosubstituted by fluorine, chlorine, bromine, nitro, methyl, methoxy or trifluoromethyl, and at least one active compound of the formula (II).

Especially preferred are active compound combinations comprising the compound of the formula (I-1)

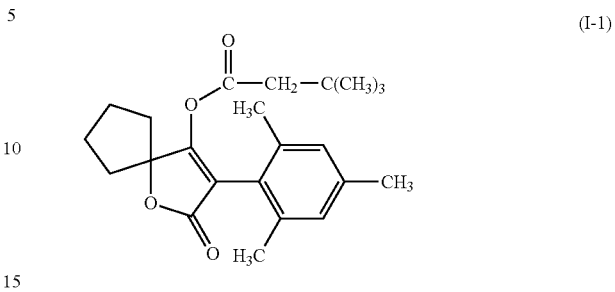

(I-1)

and at least one active compound of the formula (II).

Especially preferred are active compound combinations comprising the compound of the formula (I-2)

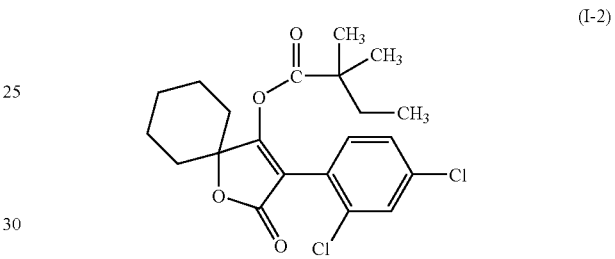

(I-2)

and at least one active compound of the formula (II).

Depending inter alia on the nature of the substituents, the compounds of the formula (I) may be present as geometrical and/or optical isomers or isomer mixtures of varying composition which, if appropriate, may be separated in a customary manner. The present invention provides both the pure isomers and the isomer mixtures, their preparation and use and also compositions comprising them. However, hereinbelow, for the sake of simplicity, only compounds of the formula (I) are referred to, although what is meant are both the pure compounds and, if appropriate, also mixtures having varying proportions of isomeric compounds.

Especially preferred are active compound combinations comprising a compound selected from the group of compounds (2-1) to (2-29) of group 2 and at least one active compound of the formula (II).

Emphasis is given to active compound combinations comprising one of the compounds (2-2) abamectin, (2-5) diafenthiuron, (2-17) spinosad and (2-20) endosulfan and at least one active compound of the formula (II).

The anthranilamides of the formula (II) are likewise known compounds which are known from the following publications or embraced by them:

WO 01/70671, WO 03/015518, WO 03/015519, WO 03/016284, WO 03/016282, WO 03/016283, WO 03/024222, WO 03/062226.

The generic formulae and definitions described in these publications and the individual compounds described therein are expressly incorporated into the present application by way of reference.

The anthranilamides can be summarized under the formula (II):

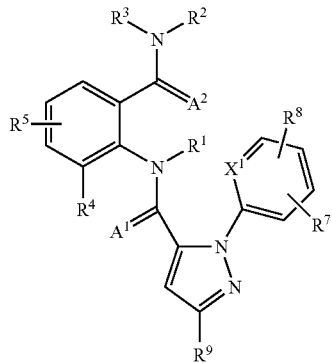

in which
A$^1$ and A$^2$ independently of one another represent oxygen or sulfur,
X$^1$ represents N or CR$^{10}$,
R$^1$ represents hydrogen or represents in each case optionally mono- or polysubstituted C$_1$-C$_6$-alkyl, C$_2$-C$_6$-alkenyl, C$_2$-C$_6$-alkynyl or C$_3$-C$_6$-cycloalkyl, where the substituents independently of one another may be selected from the group consisting of R$^6$, halogen, cyano, nitro, hydroxyl, C$_1$-C$_4$-alkoxy, C$_1$-C$_4$-alkylthio, C$_1$-C$_4$-alkylsulfinyl, C$_1$-C$_4$-alkylsulfonyl, C$_2$-C$_4$-alkoxycarbonyl, C$_1$-C$_4$-alkylamino, C$_2$-C$_8$-dialkylamino, C$_3$-C$_6$-cyclo-alkylamino, (C$_1$-C$_4$-alkyl)C$_3$-C$_6$-cycloalkylamino and R$^{11}$,
R$^2$ represents hydrogen, C$_1$-C$_6$-alkyl, C$_2$-C$_6$-alkenyl, C$_2$-C$_6$-alkynyl, C$_3$-C$_6$-cycloalkyl, C$_1$-C$_4$-alkoxy, C$_1$-C$_4$-alkylamino, C$_2$-C$_8$-dialkylamino, C$_3$-C$_6$-cycloalkylamino, C$_2$-C$_6$-alkoxycarbonyl or C$_2$-C$_6$-alkylcarbonyl,
R$^3$ represents hydrogen, R$^{11}$ or represents in each case optionally mono- or polysubstituted C$_1$-C$_6$-alkyl, C$_2$-C$_6$-alkenyl, C$_2$-C$_6$-alkynyl, C$_3$-C$_6$-cycloalkyl, where the substituents independently of one another may be selected from the group consisting of R$^6$, halogen, cyano, nitro, hydroxyl, C$_1$-C$_4$-alkoxy, C$_1$-C$_4$-haloalkoxy, C$_1$-C$_4$-alkylthio, C$_1$-C$_4$-alkylsulfinyl, C$_1$-C$_4$-alkylsulfonyl, C$_2$-C$_6$-alkoxycarbonyl, C$_2$-C$_6$-alkylcarbonyl, C$_3$-C$_6$-trialkylsilyl, R$^{11}$, phenyl, phenoxy and a 5- or 6-membered heteroaromatic ring, where each phenyl, phenoxy and 5- or 6-membered heteroaromatic ring may optionally be substituted and where the substituents independently of one another may be selected from one to three radicals W or one or more radicals R$^{12}$, or
R$^2$ and R$^3$ may be attached to one another and form the ring M,
R$^4$ represents hydrogen, C$_1$-C$_6$-alkyl, C$_2$-C$_6$-alkenyl, C$_2$-C$_6$-alkynyl, C$_3$-C$_6$-cycloalkyl, C$_1$-C$_6$-haloalkyl, C$_2$-C$_6$-haloalkenyl, C$_2$-C$_6$-haloalkynyl, C$_3$-C$_6$-halocycloalkyl, halogen, cyano, nitro, hydroxyl, C$_1$-C$_4$-alkoxy, C$_1$-C$_4$-haloalkoxy, C$_1$-C$_4$-alkylthio, C$_1$-C$_4$-alkylsulfinyl, C$_1$-C$_4$-alkylsulfonyl, C$_1$-C$_4$-haloalkylthio, C$_1$-C$_4$-haloalkylsulfinyl, C$_1$-C$_4$-haloalkylsulfonyl, C$_1$-C$_4$-alkylamino, C$_2$-C$_8$-dialkylamino, C$_3$-C$_6$-cycloalkylamino, C$_3$-C$_6$-trialkylsilyl or represents in each case optionally mono- or polysubstituted phenyl, benzyl or phenoxy, where the substituents independently of one another may be selected from the group consisting of C$_1$-C$_4$-alkyl, C$_2$-C$_4$-alkenyl, C$_2$-C$_4$-alkynyl, C$_3$-C$_6$-cycloalkyl, C$_1$-C$_4$-haloalkyl, C$_2$-C$_4$-haloalkenyl, C$_2$-C$_4$-haloalkynyl, C$_3$-C$_6$-halocycloalkyl, halogen, cyano, nitro, C$_1$-C$_4$-alkoxy, C$_1$-C$_4$-haloalkoxy, C$_1$-C$_4$-alkylthio, C$_1$-C$_4$-alkylsulfinyl, C$_1$-C$_4$-alkylsulfonyl, C$_1$-C$_4$-alkylamino, C$_2$-C$_8$-dialkylamino, C$_3$-C$_6$-cycloalkylamino, C$_3$-C$_6$-(alkyl)cycloalkylamino, C$_2$-C$_4$-alkylcarbonyl, C$_2$-C$_6$-alkoxycarbonyl, C$_2$-C$_6$-alkylaminocarbonyl, C$_3$-C$_8$-dialkylaminocarbonyl and C$_3$-C$_6$-trialkylsilyl,
R$^5$ and R$^8$ in each case independently of one another represent hydrogen, halogen or represent in each case optionally substituted C$_1$-C$_4$-alkyl, C$_1$-C$_4$-haloalkyl, R$^{12}$, G, J, —OJ, —OG, —S(O)$_p$-J, —S(O)$_p$-G, —S(O)$_p$-phenyl, where the substituents independently of one another may be selected from one to three radicals W or from the group consisting of R$^{12}$, C$_1$-C$_{10}$-alkyl, C$_2$-C$_6$-alkenyl, C$_2$-C$_6$-alkynyl, C$_1$-C$_4$-alkoxy and C$_1$-C$_4$-alkythio, where each substituent may be substituted by one or more substituents independently of one another selected from the group consisting of G, J, R$^6$, halogen, cyano, nitro, amino, hydroxyl, C$_1$-C$_4$-alkoxy, C$_1$-C$_4$-haloalkoxy, C$_1$-C$_4$-alkylthio, C$_1$-C$_4$-alkylsulfinyl, C$_1$-C$_4$-alkylsulfonyl, C$_1$-C$_4$-haloalkylthio, C$_1$-C$_4$-haloalkylsulfinyl, C$_1$-C$_4$-haloalkylsulfonyl, C$_1$-C$_4$-alkylamino, C$_2$-C$_8$-dialkylamino, C$_3$-C$_6$-trialkylsilyl, phenyl and phenoxy, where each phenyl or phenoxy ring may optionally be substituted and where the substituents independently of one another may be selected from one to three radicals W or one or more radicals R$^{12}$,
G in each case independently of one another represents a 5- or 6-membered nonaromatic carbocyclic or heterocyclic ring which optionally contains one or two ring members from the group consisting of C(=O), SO and S(=O)$_2$ and which may optionally be substituted by one to four substituents independently of one another selected from the group consisting of C$_1$-C$_2$-alkyl, halogen, cyano, nitro and C$_1$-C$_2$-alkoxy, or independently of one another represents C$_2$-C$_6$-alkenyl, C$_2$-C$_6$-alkynyl, C$_3$-C$_7$-cycloalkyl, (cyano) C$_3$-C$_7$-cycloalkyl, (C$_1$-C$_4$-alkyl)C$_3$-C$_6$-cycloalkyl, (C$_3$-C$_6$-cycloalkyl)C$_1$-C$_4$-alkyl, where each cycloalkyl, (alkyl)cycloalkyl and (cycloalkyl)alkyl may optionally be substituted by one or more halogen atoms,
J in each case independently of one another represents an optionally substituted 5- or 6-membered heteroaromatic ring, where the substituents independently of one another may be selected from one to three radicals W or one or more radicals R$^{12}$,
R$^6$ independently of one another represent —C(=E$^1$)R$^{19}$, -LC(=E$^1$)R$^{19}$, —C(=E$^1$)LR$^{19}$, -LC(=E$^1$)LR$^{19}$, —OP(=Q)(OR$^{19}$)$_2$, —SO$_2$LR$^{18}$ or -LSO$_2$LR$^{19}$, where each E$^1$ independently of the others represents O, S, N—R$^{15}$, N—OR$^{15}$, N—N(R$^{15}$)$_2$, N—S=O, N—CN or N—NO$_2$,
R$^7$ represents hydrogen, C$_1$-C$_4$-alkyl, C$_1$-C$_4$-haloalkyl, halogen, C$_1$-C$_4$-alkoxy, C$_1$-C$_4$-haloalkoxy, C$_1$-C$_4$-alkylthio, C$_1$-C$_4$-alkylsulfinyl, C$_1$-C$_4$-alkylsulfonyl, C$_1$-C$_4$-haloalkylthio, C$_1$-C$_4$-haloalkylsulfinyl, C$_1$-C$_4$-haloalkylsulfonyl,
R$^9$ represents C$_1$-C$_4$-haloalkyl, C$_1$-C$_4$-haloalkoxy, C$_1$-C$_4$-haloalkylsulfinyl or halogen,
R$^{10}$ represents hydrogen, C$_1$-C$_4$-alkyl, C$_1$-C$_4$-haloalkyl, halogen, cyano or C$_1$-C$_4$-haloalkoxy,
R$^{11}$ in each case independently of one another represents in each case optionally mono- to trisubstituted C$_1$-C$_6$-alkylthio, C$_1$-C$_6$-alkylsulfenyl, C$_1$-C$_6$-haloalkythio, C$_1$-C$_6$-haloalkylsulfenyl, phenylthio or phenylsulfenyl, where the substituents independently of one another may be selected from the list consisting of W, —S(O)$_n$N(R$^{16}$)$_2$, —C(=O)R$^{13}$, -L(C=O)R$^{14}$, —S(C=O)LR$^{14}$, —C(=O)LR$^{13}$, —S(O)$_n$NR$^{13}$C(=O)R$^{13}$, —S(O)$_n$NR$^{13}$C(=O)LR$^{14}$ and —S(O)$_n$NR$^{13}$S(O)$_2$LR$^{14}$, L in each case independently of one another represents O, $NR^{18}$ or S, $R^{12}$ in each case independently of one another represents —$B(OR^{17})_2$, amino, SH, thiocyanato, $C_3$-$C_8$-trialkylsilyloxy, $C_1$-$C_4$-alkyl disulfide, —$SF_5$, —$C(=E^1)R^{19}$, -LC$(=E^1)R^{19}$, —$C(=E^1)LR^{19}$, -LC$(=E^1)LR^{19}$, —$OP(=Q)(OR^{19})_2$, —$SO_2LR^{19}$ or -$LSO_2LR^{19}$, Q represents O or S, $R^{13}$ in each case independently of one another represents hydrogen or represents in each case optionally mono- or polysubstituted $C_1$-$C_6$-alkyl, $C_2$-$C_6$-alkenyl, $C_2$-$C_6$-alkynyl or $C_3$-$C_6$-cycloalkyl, where the substituents independently of one another may be selected from the group consisting of $R^6$, halogen, cyano, nitro, hydroxyl, $C_1$-$C_4$-alkoxy, $C_1$-$C_4$-alkylsulfinyl, $C_1$-$C_4$-alkylsulfonyl, $C_1$-$C_4$-alkylamino, $C_2$-$C_8$-dialkylamino, $C_3$-$C_6$-cycloalkylamino and ($C_1$-$C_4$-alkyl)$C_3$-$C_6$-cycloalkylamino, $R^{14}$ in each case independently of one another represents in each case optionally mono- or polysubstituted $C_1$-$C_{20}$-alkyl, $C_2$-$C_{20}$-alkenyl, $C_2$-$C_{20}$-alkynyl or $C_3$-$C_6$-cycloalkyl, where the substituents independently of one another may be selected from the group consisting of $R^6$, halogen, cyano, nitro, hydroxyl, $C_1$-$C_4$-alkoxy, $C_1$-$C_4$-alkylsulfinyl, $C_1$-$C_4$-alkylsulfonyl, $C_1$-$C_4$-alkylamino, $C_2$-$C_8$-dialkylamino, $C_3$-$C_6$-cycloalkylamino and ($C_1$-$C_4$-alkyl)$C_3$-$C_6$-cycloalkylamino or represents optionally substituted phenyl, where the substituents independently of one another may be selected from one to three radicals W or one or more radicals $R^{12}$, $R^{15}$ in each case independently of one another represents hydrogen or represents in each case mono- or polysubstituted $C_1$-$C_6$-haloalkyl or $C_1$-$C_6$-alkyl, where the substituents independently of one another may be selected from the group consisting of cyano, nitro, hydroxyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, $C_1$-$C_4$-alkylamino, $C_2$-$C_8$-dialkylamino, $C_2$-$C_6$-alkoxycarbonyl, $C_2$-$C_6$-alkylcarbonyl, $C_3$-$C_6$-trialkylsilyl and optionally substituted phenyl, where the substituents independently of one another may be selected from one to three radicals W or one or more radicals $R^{12}$, or $N(R^{15})_2$ represents a cycle which forms the ring M, $R^{16}$ represents $C_1$-$C_{12}$-alkyl or $C_1$-$C_{12}$-haloalkyl, or $N(R^{16})_2$ represents a cycle which forms the ring M, $R^{17}$ in each case independently of one another represents hydrogen or $C_1$-$C_4$-alkyl, or $B(OR^{17})_2$ represents a ring, where the two oxygen atoms are attached via a chain to two or three, carbon atoms which are optionally substituted by one or two substituents independently of one another selected from the group consisting of methyl and $C_2$-$C_6$-alkoxycarbonyl, $R^{18}$ in each case independently of one another represents hydrogen, $C_1$-$C_6$-alkyl or $C_1$-$C_6$-haloalkyl, or $N(R^{13})(R^{18})$ represents a cycle which forms the ring M, $R^{19}$ in each case independently of one another represents hydrogen or represents in each case optionally mono- or polysubstituted $C_1$-$C_6$-alkyl, where the substituents independently of one another may be selected from the group consisting of cyano, nitro, hydroxyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, $C_1$-$C_4$-alkylamino, $C_2$-$C_8$-dialkylamino, $CO_2H$, $C_2$-$C_6$-alkoxycarbonyl, $C_2$-$C_6$-alkylcarbonyl, $C_3$-$C_6$-trialkylsilyl and optionally substituted phenyl, where the substituents independently of one another may be selected from one to three radicals W, $C_1$-$C_6$-haloalkyl, $C_3$-$C_6$-cycloalkyl or phenyl or pyridyl, each of which is optionally mono- to trisubstituted by W, M in each case represents an optionally mono- to tetrasubstituted ring which, in addition to the nitrogen atom which is attached to the substituent pair $R^{13}$ and $R^{18}$, $(R^{15})_2$ or $(R^{16})_2$, contains two to six carbon atoms and optionally additionally a further nitrogen, sulfur or oxygen atom, and where the substituents independently of one another may be selected from the group consisting of $C_1$-$C_2$-alkyl, halogen, cyano, nitro and $C_1$-$C_2$-alkoxy, W in each case independently of one another represent $C_1$-$C_4$-alkyl, $C_2$-$C_4$-alkenyl, $C_2$-$C_4$-alkynyl, $C_3$-$C_6$-cycloalkyl, $C_1$-$C_4$-haloalkyl, $C_2$-$C_4$-haloalkenyl, $C_2$-$C_4$-haloalkynyl, $C_3$-$C_6$-halocycloalkyl, halogen, cyano, nitro, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylamino, $C_2$-$C_8$-dialkylamino, $C_3$-$C_6$-cycloalkylamino, ($C_1$-$C_4$-alkyl)$C_3$-$C_6$-cycloalkylamino, $C_2$-$C_4$-alkylcarbonyl, $C_2$-$C_6$-alkoxy-carbonyl, $CO_2H$, $C_2$-$C_6$-alkylaminocarbonyl, $C_3$-$C_8$-dialkylaminocarbonyl or $C_3$-$C_6$-trialkylsilyl, n in each case independently of one another represents 0 or 1, p in each case independently of one another represents 0, 1 or 2.

If (a) $R^5$ represents hydrogen, $C_1$-$C_6$-alkyl, $C_1$-$C_6$-haloalkyl, $C_2$-$C_6$-haloalkenyl, $C_2$-$C_6$-haloalkynyl, $C_1$-$C_4$-haloalkoxy, $C_1$-$C_4$-haloalkylthio or halogen and (b) $R^8$ represents hydrogen, $C_1$-$C_6$-alkyl, $C_1$-$C_6$-haloalkyl, $C_2$-$C_6$-haloalkenyl, $C_2$-$C_6$-haloalkynyl, $C_1$-$C_4$-haloalkoxy, $C_1$-$C_4$-haloalkylthio, halogen, $C_2$-$C_4$-alkylcarbonyl, $C_2$-$C_6$-alkoxycarbonyl, $C_2$-$C_6$-alkylaminocarbonyl or $C_3$-$C_8$ dialkylaminocarbonyl, (c) at least one substituent selected from the group consisting of $R^6$, $R^{11}$ and $R^{12}$ is present and (d), if $R^{12}$ is not present, at least one $R^6$ or $R^{11}$ is different from $C_2$-$C_6$-alkylcarbonyl, $C_2$-$C_6$ alkoxycarbonyl, $C_2$-$C_6$-alkylaminocarbonyl and $C_3$-$C_8$-dialkylaminocarbonyl.

The compounds of the general formula (II) include N-oxides and salts.

Depending inter alia on the nature of the substituents, the compounds of the formula (II) may be present as geometrical and/or optical isomers or isomer mixtures of varying composition which, if appropriate, may be separated in a customary manner. The present invention provides both the pure isomers and the isomer mixtures, their preparation and use and also compositions comprising them. However, hereinbelow, for the sake of simplicity, only compounds of the formula (II) are referred to, although what is meant are both the pure compounds and, if appropriate, also mixtures having varying proportions of isomeric compounds.

Preference is given to active compound combinations comprising compounds of the formula (II-1)

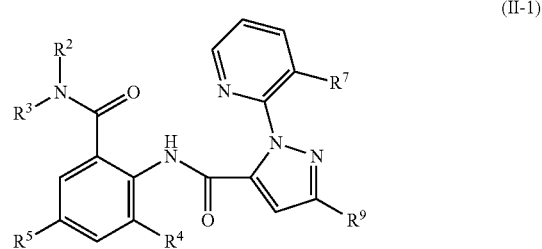

in which

R² represents hydrogen or C₁-C₆-alkyl,

R³ represents C₁-C₆-alkyl which is optionally substituted by a radical R⁶,

R⁴ represents C₁-C₄-alkyl, C₁-C₂-haloalkyl, C₁-C₂-haloalkoxy or halogen,

R⁵ represents hydrogen, C₁-C₄-alkyl, C₁-C₂-haloalkyl, C₁-C₂-haloalkoxy or halogen, R⁶ represents —C(=E²)R¹⁹, -LC(=E²)R¹⁹, —C(=E²)LR¹⁹ or -LC(=E²)LR¹⁹, where each E² independently of the others represents O, S, N—R¹⁵, N—OR¹⁵, N—N(R⁵)₂, and each L independently of the others represents O or NR¹⁸, R⁷ represents C₁-C₄-haloalkyl or halogen, R⁹ represents C₁-C₂-haloalkyl, C₁-C₂-haloalkoxy, S(O)$_p$C₁-C₂-haloalkyl or halogen, R¹⁵ in each case independently of one another represents hydrogen or represents in each case optionally substituted C₁-C₆-haloalkyl or C₁-C₆-alkyl, where the substituents independently of one another may be selected from the group consisting of cyano, C₁-C₄-alkoxy, C₁-C₄-haloalkoxy, C₁-C₄-alkylthio, C₁-C₄-alkylsulfinyl, C₁-C₄-alkylsulfonyl, C₁-C₄-haloalkylthio, C₁-C₄-haloalkylsulfinyl or C₁-C₄-haloalkylsulfonyl, R¹⁸ in each case represents hydrogen or C₁-C₄-alkyl, R¹⁹ in each case independently of one another represents hydrogen or C₁-C₆-alkyl, p independently of one another represents 0, 1, 2.

In the radical definitions mentioned as being preferred, halogen represents fluorine, chlorine, bromine and iodine, in particular fluorine, chlorine and bromine.

Particular preference is given to active compound combinations comprising compounds of the formula (II-1), in which R² represents hydrogen or methyl, R³ represents C₁-C₄-alkyl (in particular methyl, ethyl, n-, isopropyl, n-, iso-, sec-, tert-butyl), R⁴ represents methyl, trifluoromethyl, trifluoromethoxy, fluorine, chlorine, bromine or iodine, R⁵ represents hydrogen, fluorine, chlorine, bromine, iodine, trifluoromethyl or trifluoromethoxy, R⁷ represents chlorine or bromine, R⁹ represents trifluoromethyl, chlorine, bromine, difluoromethoxy or trifluoroethoxy.

Very particular preference is given to active compound combinations comprising the following compounds of the formula (II-1):

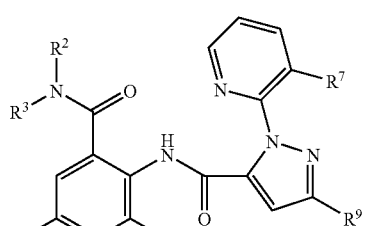

(II-1)

| Example No. | R² | R³ | R⁴ | R⁵ | R⁷ | R⁹ | m.p. (0° C.) |
|---|---|---|---|---|---|---|---|
| II-1-1 | H | Me | Me | Cl | Cl | CF₃ | 185-186 |
| II-1-2 | H | Me | Me | Cl | Cl | OCH₂CF₃ | 207-208 |
| II-1-3 | H | Me | Me | Cl | Cl | Cl | 225-226 |
| II-1-4 | H | Me | Me | Cl | Cl | Br | 162-164 |
| II-1-5 | H | Me | Cl | Cl | Cl | CF₃ | 155-157 |
| II-1-6 | H | Me | Cl | Cl | Cl | OCH₂CF₃ | 192-195 |

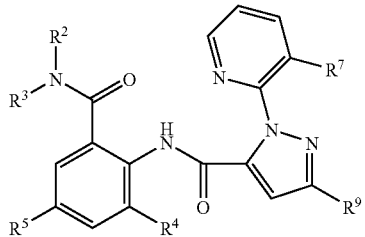

(II-1)

| Example No. | R² | R³ | R⁴ | R⁵ | R⁷ | R⁹ | m.p. (0° C.) |
|---|---|---|---|---|---|---|---|
| II-1-7 | H | Me | Cl | Cl | Cl | Cl | 205-206 |
| II-1-8 | H | Me | Cl | Cl | Cl | Br | 245-246 |
| II-1-9 | H | i-Pr | Me | Cl | Cl | CF₃ | 195-196 |
| II-1-10 | H | i-Pr | Me | Cl | Cl | OCH₂CF₃ | 217-218 |
| II-1-11 | H | i-Pr | Me | Cl | Cl | Cl | 173-175 |
| II-1-12 | H | i-Pr | Me | Cl | Cl | Br | 159-161 |
| II-1-13 | H | i-Pr | Cl | Cl | Cl | CF₃ | 200-201 |
| II-1-14 | H | i-Pr | Cl | Cl | Cl | OCH₂CF₃ | 232-235 |
| II-1-15 | H | i-Pr | Cl | Cl | Cl | Cl | 197-199 |
| II-1-16 | H | i-Pr | Cl | Cl | Cl | Br | 188-190 |
| II-1-17 | H | Et | Me | Cl | Cl | CF₃ | 163-164 |
| II-1-18 | H | Et | Me | Cl | Cl | OCH₂CF₃ | 205-207 |
| II-1-19 | H | Et | Me | Cl | Cl | Cl | 199-200 |
| II-1-20 | H | Et | Me | Cl | Cl | Br | 194-195 |
| II-1-21 | H | Et | Cl | Cl | Cl | CF₃ | 201-202 |
| II-1-22 | H | Et | Cl | Cl | Cl | Cl | 206-208 |
| II-1-23 | H | Et | Cl | Cl | Cl | Br | 214-215 |
| II-1-24 | H | t-Bu | Me | Cl | Cl | CF₃ | 223-225 |
| II-1-25 | H | t-Bu | Me | Cl | Cl | Cl | 163-165 |
| II-1-26 | H | t-Bu | Me | Cl | Cl | Br | 159-161 |
| II-1-27 | H | t-Bu | Cl | Cl | Cl | CF₃ | 170-172 |
| II-1-28 | H | t-Bu | Cl | Cl | Cl | Cl | 172-173 |
| II-1-29 | H | t-Bu | Cl | Cl | Cl | Br | 179-180 |
| II-1-30 | H | Me | Me | Br | Cl | CF₃ | 222-223 |
| II-1-31 | H | Et | Me | Br | Cl | CF₃ | 192-193 |
| II-1-32 | H | i-Pr | Me | Br | Cl | CF₃ | 197-198 |
| II-1-33 | H | t-Bu | Me | Br | Cl | CF₃ | 247-248 |
| II-1-34 | H | Me | Me | Br | Cl | Cl | 140-141 |
| II-1-35 | H | Et | Me | Br | Cl | Cl | 192-194 |
| II-1-36 | H | i-Pr | Me | Br | Cl | Cl | 152-153 |
| II-1-37 | H | t-Bu | Me | Br | Cl | Cl | 224-225 |
| II-1-38 | H | Me | Me | Br | Cl | Br | 147-149 |
| II-1-39 | H | Et | Me | Br | Cl | Br | 194-196 |
| II-1-40 | H | i-Pr | Me | Br | Cl | Br | 185-187 |
| II-1-41 | H | t-Bu | Me | Br | Cl | Br | 215-221 |
| II-1-42 | H | Me | Me | I | Cl | CF₃ | 199-200 |
| II-1-43 | H | Et | Me | I | Cl | CF₃ | 199-200 |
| II-1-44 | H | i-Pr | Me | I | Cl | CF₃ | 188-189 |
| II-1-45 | H | t-Bu | Me | I | Cl | CF₃ | 242-243 |
| II-1-46 | H | Me | Me | I | Cl | Cl | 233-234 |
| II-1-47 | H | Et | Me | I | Cl | Cl | 196-197 |
| II-1-48 | H | i-Pr | Me | I | Cl | Cl | 189-190 |
| II-1-49 | H | t-Bu | Me | I | Cl | Cl | 228-229 |
| II-1-50 | H | Me | Me | I | Cl | Br | 229-230 |
| II-1-51 | H | iPr | Me | I | Cl | Br | 191-192 |
| II-1-52 | H | Me | Br | Br | Cl | CF₃ | 162-163 |
| II-1-53 | H | Et | Br | Br | Cl | CF₃ | 188-189 |
| II-1-54 | H | i-Pr | Br | Br | Cl | CF₃ | 192-193 |
| II-1-55 | H | t-Bu | Br | Br | Cl | CF₃ | 246-247 |
| II-1-56 | H | Me | Br | Br | Cl | Cl | 188-190 |
| II-1-57 | H | Et | Br | Br | Cl | Cl | 192-194 |
| II-1-58 | H | i-Pr | Br | Br | Cl | Cl | 197-199 |
| II-1-59 | H | t-Bu | Br | Br | Cl | Cl | 210-212 |
| II-1-60 | H | Me | Br | Br | Cl | Br | 166-168 |
| II-1-61 | H | Et | Br | Br | Cl | Br | 196-197 |
| II-1-62 | H | i-Pr | Br | Br | Cl | Br | 162-163 |
| II-1-63 | H | t-Bu | Br | Br | Cl | Br | 194-196 |
| II-1-64 | H | t-Bu | Cl | Br | Cl | CF₃ | 143-145 |
| II-1-65 | Me | Me | Br | Br | Cl | Cl | 153-155 |
| II-1-66 | Me | Me | Me | Br | Cl | CF₃ | 207-208 |
| II-1-67 | Me | Me | Cl | Cl | Cl | Cl | 231-232 |
| II-1-68 | Me | Me | Br | Br | Cl | Br | 189-190 |
| II-1-69 | Me | Me | Cl | Cl | Cl | Br | 216-218 |
| II-1-70 | Me | Me | Cl | Cl | Cl | CF₃ | 225-227 |
| II-1-71 | Me | Me | Br | Br | Cl | CF₃ | 228-229 |

-continued
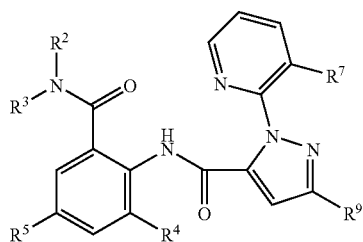
(II-1)
| Example No. | R² | R³ | R⁴ | R⁵ | R⁷ | R⁹ | m.p. (0° C.) |
|---|---|---|---|---|---|---|---|
| II-1-72 | H | i-Pr | Me | H | Cl | CF₃ | 237-239 |
Especially preferred are active compound combinations comprising a compound of the formulae below
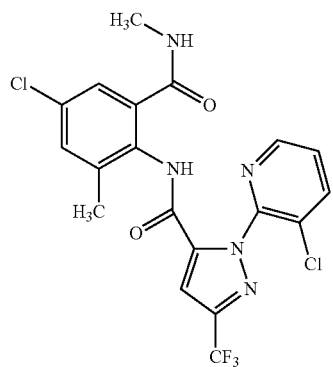
(II-1-1)
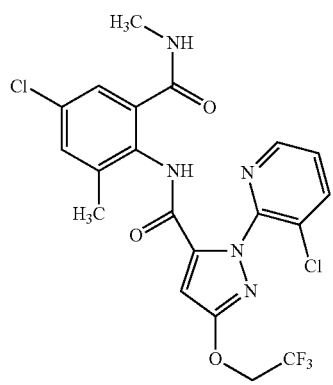
(II-1-2)
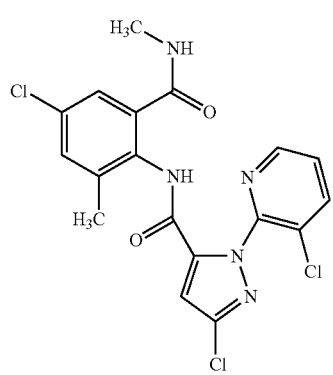
(II-1-3)
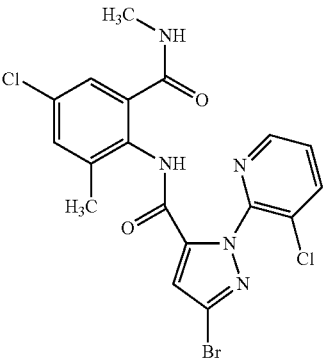
(II-1-4)
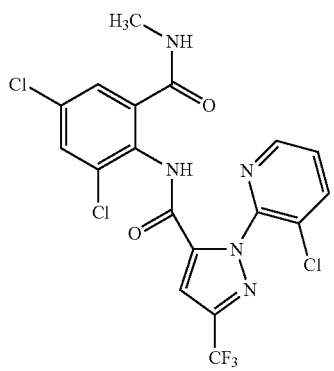
(II-1-5)
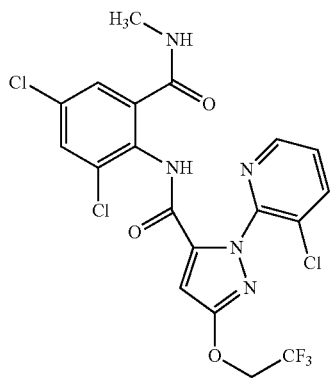
(II-1-6)
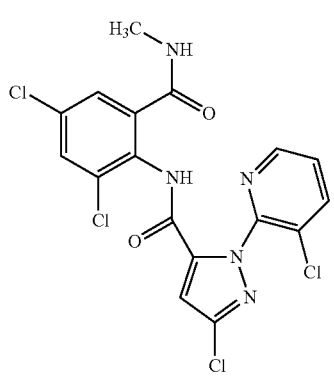
(II-1-7)

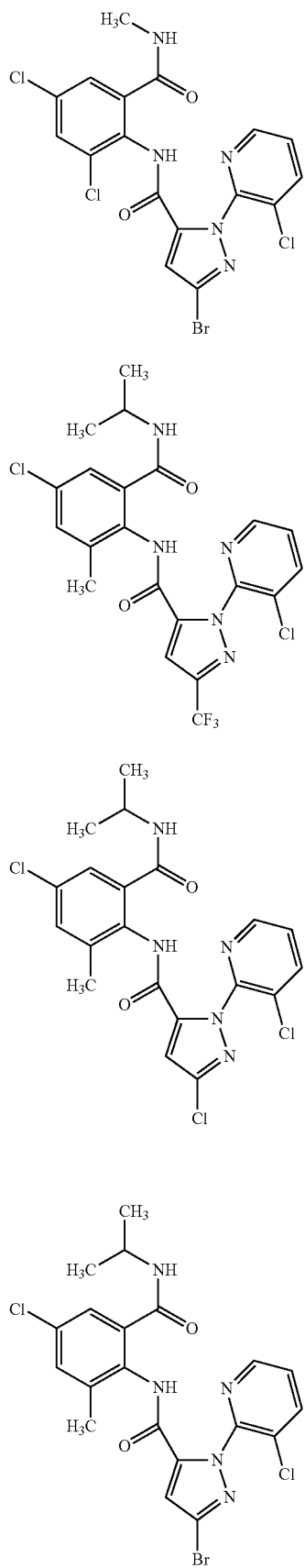
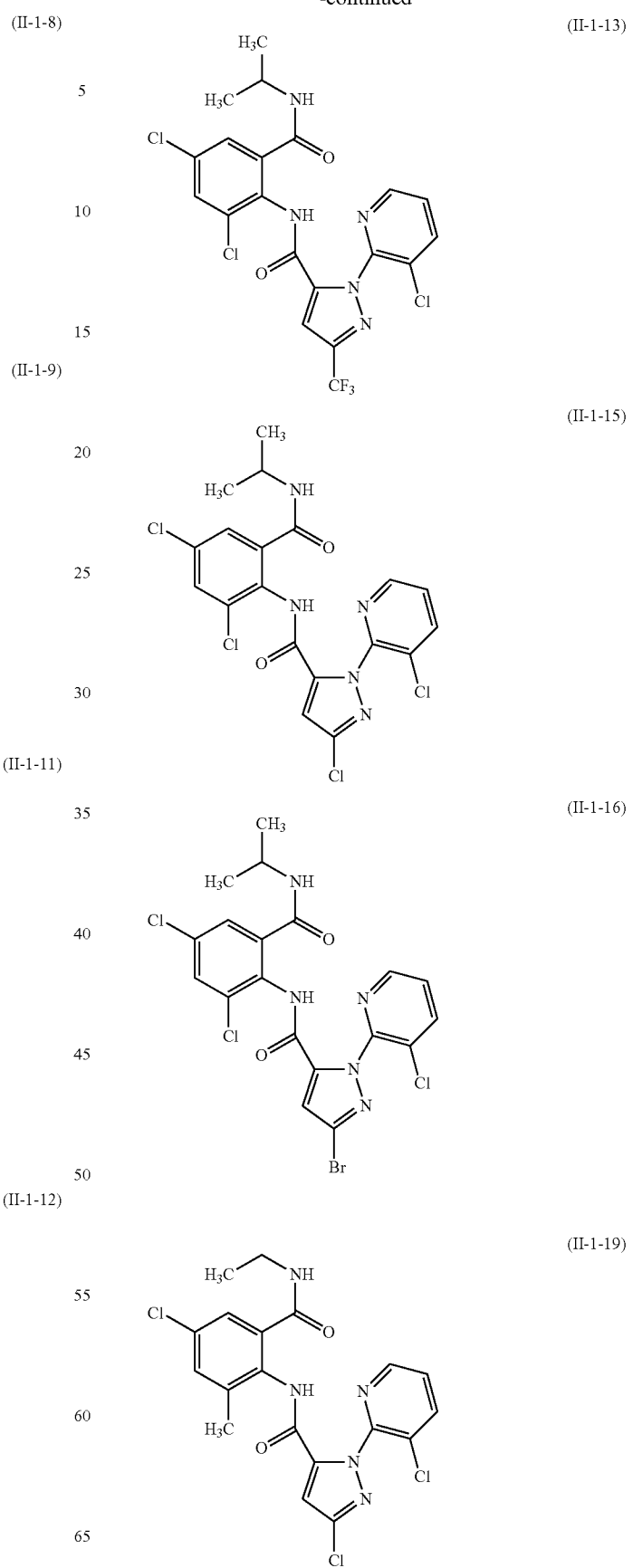

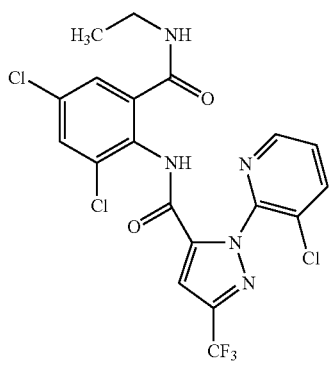 (II-1-21)
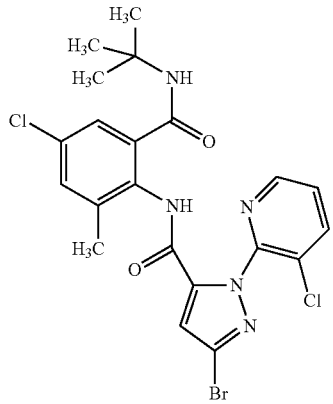 (II-1-26)
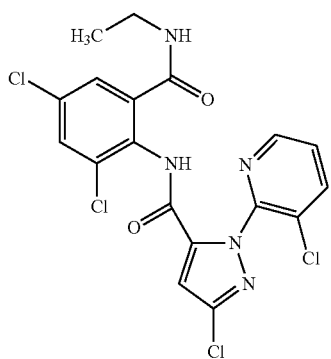 (II-1-22)
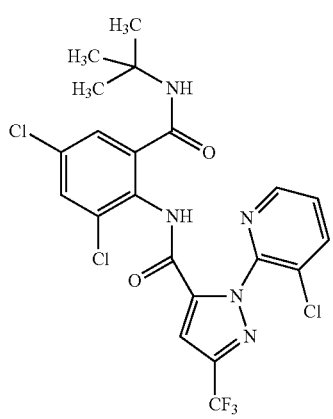 (II-1-27)
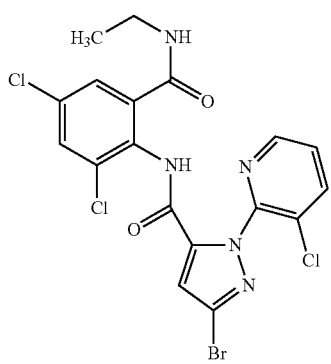 (II-1-23)
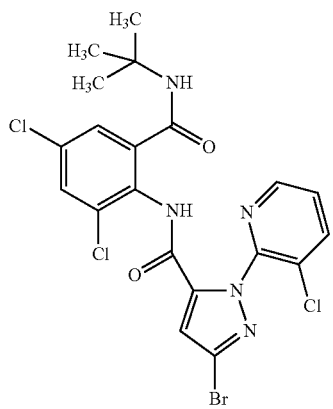 (II-1-29)
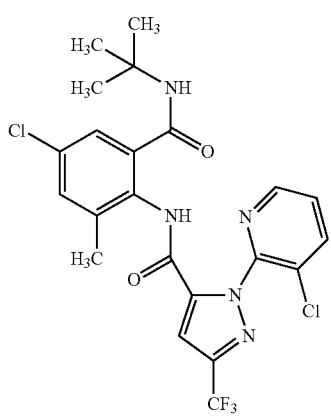 (II-1-24)
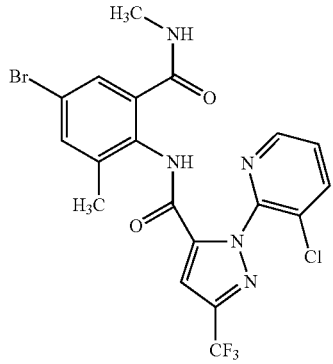 (II-1-30)

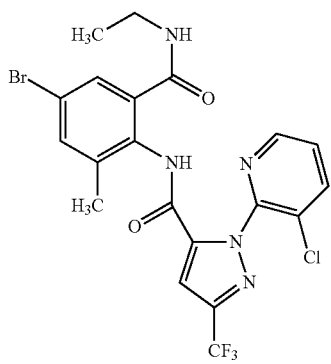
(II-1-31)
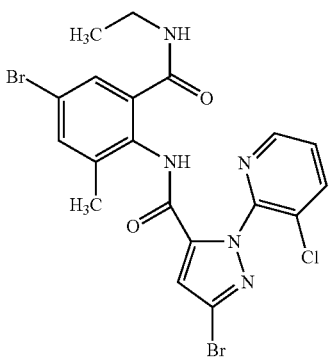
(II-1-39)
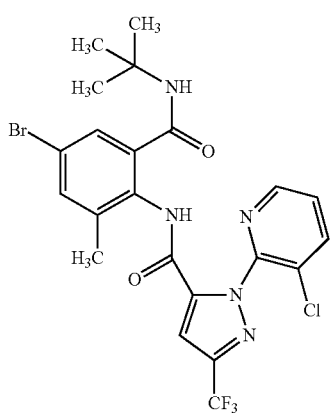
(II-1-32)
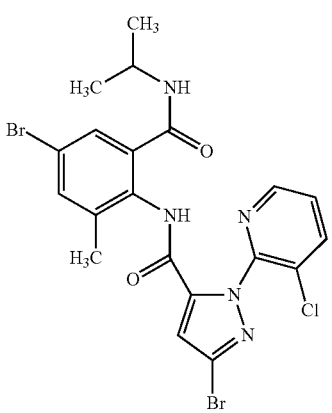
(II-1-40)
(II-1-33)
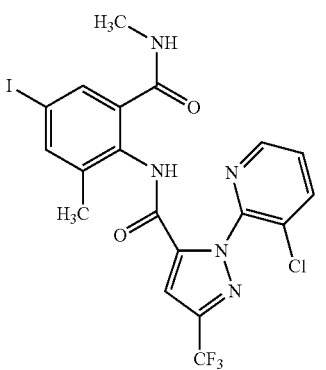
(II-1-42)
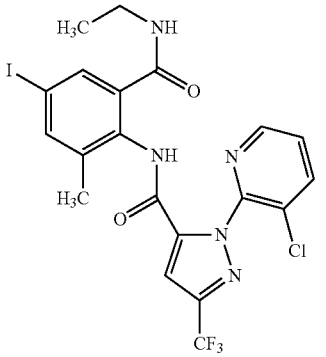
(II-1-38)
(II-1-43)

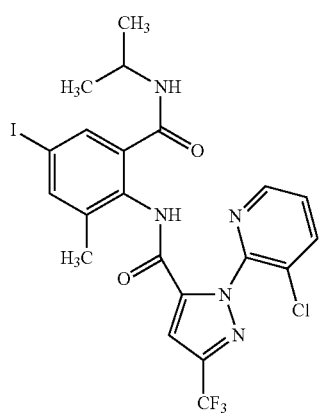
(II-1-44)
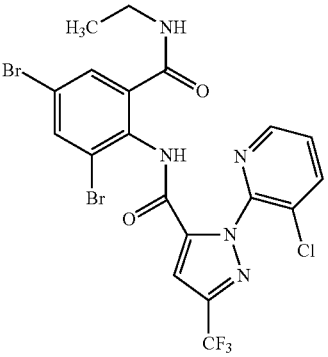
(II-1-53)
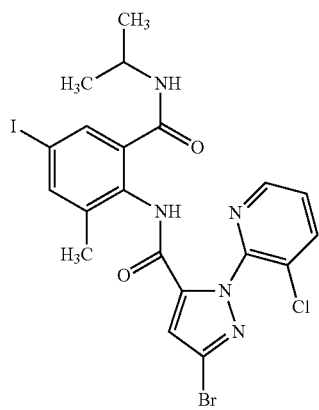
(II-1-50)
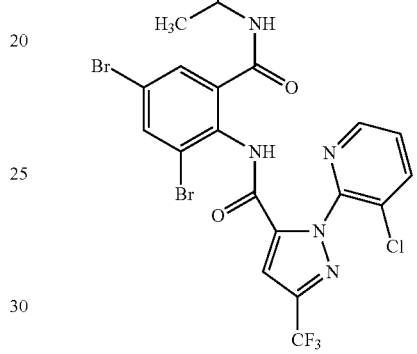
(II-1-54)
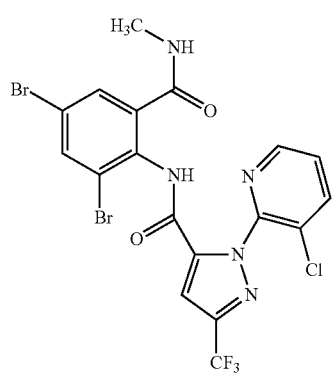
(II-1-51)
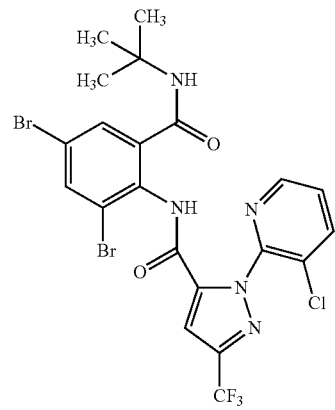
(II-1-55)
(II-1-52)
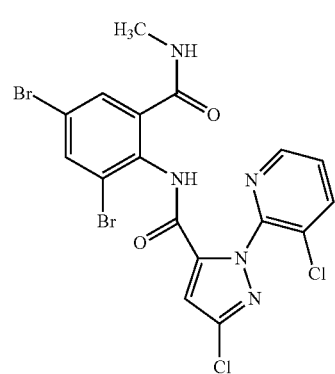
(II-1-56)

(II-1-57)
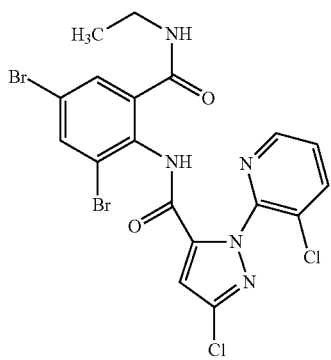
(II-1-58)
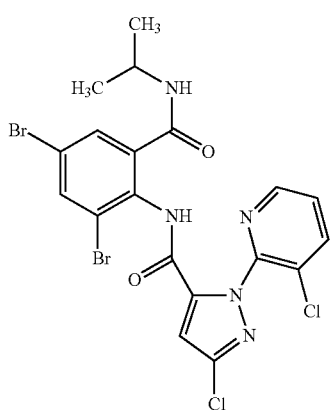
(II-1-60)
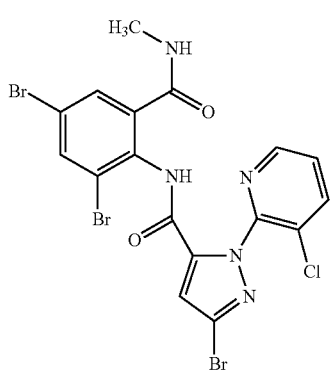
(II-1-61)
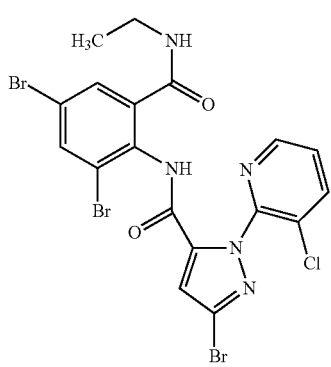
(II-1-62)
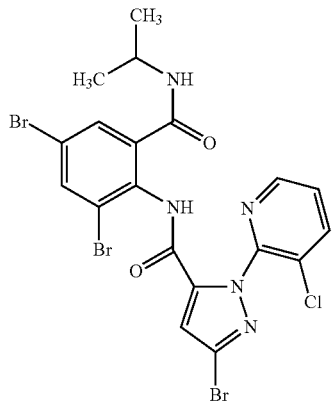
(II-1-64)
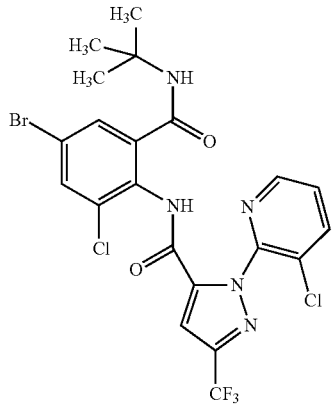
(II-1-65)
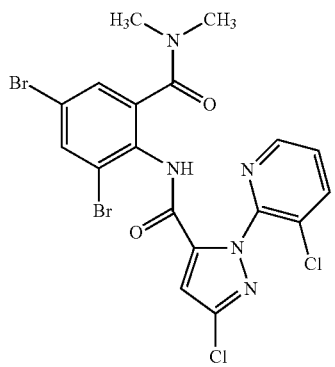
(II-1-66)
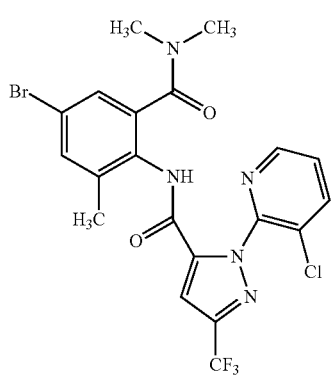

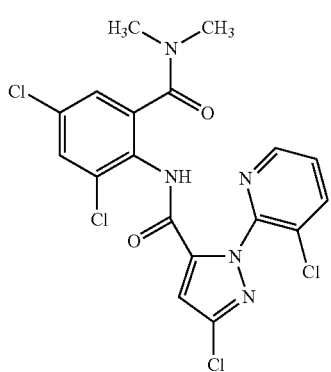 (II-1-67)

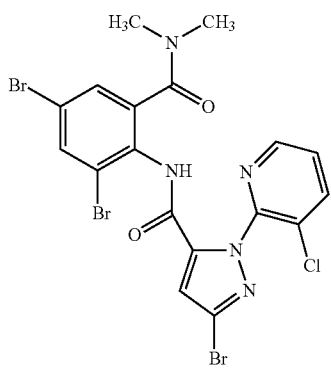 (II-1-68)

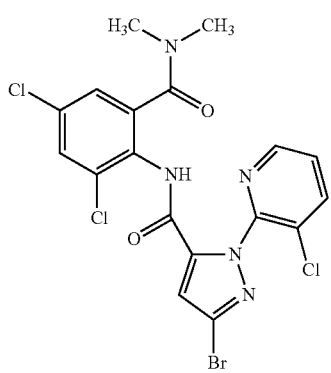 (II-1-69)

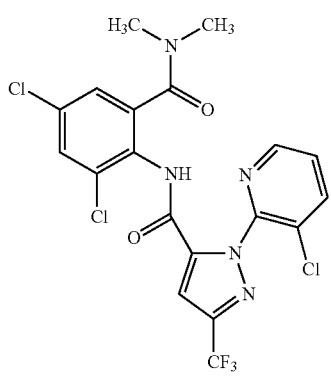 (II-1-70)

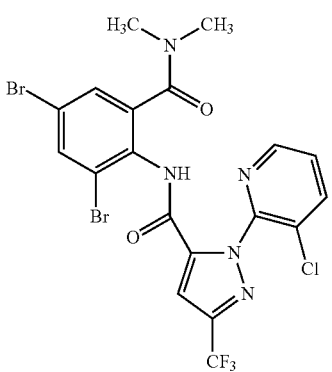 (II-1-71)

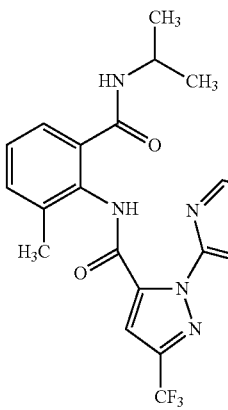 (II-1-72)

Emphasis is given to the following specifically mentioned active compound combinations (2-compound mixtures) comprising a compound of the formula (I) (group 1) or an acaricidally active compound of group 2 and a compound of the formula (II-1):

| No. | Active compound combination comprising |
|---|---|
| 1a) | (I-1) and (II-1-1) |
| 1b) | (I-2) and (11-1-1) |
| 1c) | (2-2) abamectin and (II-1-1) |
| 1d) | (2-5) diafenthiuron and (II-1-1) |
| 1e) | (2-17) spinosad and (II-1-1) |
| 1f) | (2-20) endosulfan and (II-1-1) |
| 2a) | (I-1) and (II-1-2) |
| 2b) | (I-2) and (II-1-2) |
| 2c) | (2-2) abamectin and (II-1-2) |
| 2d) | (2-5) diafenthiuron and (II-1-2) |
| 2e) | (2-17) spinosad and (II-1-2) |
| 2f) | (2-20) endosulfan and (II-1-2) |
| 3a) | (I-1) and (II-1-3) |
| 3b) | (I-2) and (II-1-3) |
| 3c) | (2-2) abamectin and (II-1-3) |
| 3d) | (2-5) diafenthiuron and (II-1-3) |
| 3e) | (2-17) spinosad and (II-1-3) |
| 3f) | (2-20) endosulfan and (II-1-3) |
| 4a) | (I-1) and (II-1-4) |
| 4b) | (I-2) and (II-1-4) |
| 4c) | (2-2) abamectin and (II-1-4) |
| 4d) | (2-5) diafenthiuron and (II-1-4) |
| 4e) | (2-17) spinosad and (II-1-4) |
| 4f) | (2-20) endosulfan and (II-1-4) |
| 5a) | (I-1) and (II-1-5) |
| 5b) | (I-2) and (II-1-5) |
| 5c) | (2-2) abamectin and (II-1-5) |
| 5d) | (2-5) diafenthiuron and (II-1-5) |

-continued

| No. | Active compound combination comprising |
|---|---|
| 5e) | (2-17) spinosad and (II-1-5) |
| 5f) | (2-20) endosulfan and (II-1-5) |
| 6a) | (I-1) and (II-1-6) |
| 6b) | (I-2) and (II-1-6) |
| 6c) | (2-2) abamectin and (II-1-6) |
| 6d) | (2-5) diafenthiuron and (II-1-6) |
| 6e) | (2-17) spinosad and (II-1-6) |
| 6f) | (2-20) endosulfan and (II-1-6) |
| 7a) | (I-1) and (II-1-7) |
| 7b) | (I-2) and (II-1-7) |
| 7c) | (2-2) abamectin and (II-1-7) |
| 7d) | (2-5) diafenthiuron and (II-1-7) |
| 7e) | (2-17) spinosad and (II-1-7) |
| 7f) | (2-20) endosulfan and (II-1-7) |
| 8a) | (I-1) and (II-1-8) |
| 8b) | (I-2) and (II-1-8) |
| 8c) | (2-2) abamectin and (II-1-8) |
| 8d) | (2-5) diafenthiuron and (II-1-8) |
| 8e) | (2-17) spinosad and (II-1-8) |
| 8f) | (2-20) endosulfan and (II-1-8) |
| 9a) | (I-1) and (II-1-9) |
| 9b) | (I-2) and (II-1-9) |
| 9c) | (2-2) abamectin and (II-1-9) |
| 9d) | (2-5) diafenthiuron and (II-1-9) |
| 9e) | (2-17) spinosad and (II-1-9) |
| 9f) | (2-20) endosulfan and (II-1-9) |
| 10a) | (I-1) and (II-1-11) |
| 10b) | (I-2) and (II-1-11) |
| 10c) | (2-2) abamectin and (II-1-11) |
| 10d) | (2-5) diafenthiuron and (II-1-11) |
| 10e) | (2-17) spinosad and (II-1-11) |
| 10t) | (2-20) endosulfan and (II-1-11) |
| 11a) | (I-1) and (II-1-12) |
| 11b) | (I-2) and (II-1-12) |
| 11c) | (2-2) abamectin and (II-1-12) |
| 11d) | (2-5) diafenthiuron and (II-1-12) |
| 11e) | (2-17) spinosad and (II-1-12) |
| 11f) | (2-20) endosulfan and (II-1-12) |
| 12a) | (I-1) and (II-1-13) |
| 12b) | (I-2) and (II-1-13) |
| 12c) | (2-2) abamectin and (II-1-13) |
| 12d) | (2-5) diafenthiuron and (II-1-13) |
| 12e) | (2-17) spinosad and (II-1-13) |
| 12f) | (2-20) endosulfan and (II-1-13) |
| 13a) | (I-1) and (II-1-15) |
| 13b) | (I-2) and (II-1-15) |
| 13c) | (2-2) abamectin and (II-1-15) |
| 13d) | (2-5) diafenthiuron and (II-1-15) |
| 13e) | (2-17) spinosad and (II-1-15) |
| 13f) | (2-20) endosulfan and (II-1-15) |
| 14a) | (I-1) and (II-1-16) |
| 14b) | (I-2) and (II-1-16) |
| 14c) | (2-2) abamectin and (II-1-16) |
| 14d) | (2-5) diafenthiuron and (II-1-16) |
| 14e) | (2-17) spinosad and (II-1-16) |
| 14f) | (2-20) endosulfan and (II-1-16) |
| 15a) | (I-1) and (II-1-19) |
| 15b) | (I-2) and (II-1-19) |
| 15c) | (2-2) abamectin and (II-1-19) |
| 15d) | (2-5) diafenthiuron and (II-1-19) |
| 15e) | (2-17) spinosad and (II-1-19) |
| 15f) | (2-20) endosulfan and (II-1-19) |
| 16a) | (I-I) and (II-1-21) |
| 16b) | (I-2) and (II-1-21) |
| 16c) | (2-2) abamectin and (II-1-21) |
| 16d) | (2-5) diafenthiuron and (II-1-21) |
| 16e) | (2-17) spinosad and (II-1-21) |
| 16f) | (2-20) endosulfan and (II-1-21) |
| 17a) | (I-1) and (II-1-22) |
| 17b) | (I-2) and (II-1-22) |
| 17c) | (2-2) abamectin and (II-1-22) |
| 17d) | (2-5) diafenthiuron and (II-1-22) |
| 17e) | (2-17) spinosad and (II-1-22) |
| 17f) | (2-20) endosulfan and (II-1-22) |
| 18a) | (I-1) and (II-1-23) |
| 18b) | (I-2) and (II-1-23) |
| 18c) | (2-2) abamectin and (II-1-23) |
| 18d) | (2-5) diafenthiuron and (II-1-23) |
| 18e) | (2-17) spinosad and (II-1-23) |
| 18f) | (2-20) endosulfan and (II-1-23) |
| 19a) | (I-1) and (II-1-24) |
| 19b) | (I-2) and (II-1-24) |
| 19c) | (2-2) abamectin and (II-1-24) |
| 19d) | (2-5) diafenthiuron and (II-1-24) |
| 19e) | (2-17) spinosad and (II-1-24) |
| 19f) | (2-20) endosulfan and (II-1-24) |
| 20a) | (I-1) and (II-1-26) |
| 20b) | (I-2) and (II-1-26) |
| 20c) | (2-2) abamectin and (II-1-26) |
| 20d) | (2-5) diafenthiuron and (II-1-26) |
| 20e) | (2-17) spinosad and (II-1-26) |
| 20f) | (2-20) endosulfan and (II-1-26) |
| 21a) | (I-1) and (II-1-27) |
| 21b) | (I-2) and (II-1-27) |
| 21c) | (2-2) abamectin and (II-1-27) |
| 21d) | (2-5) diafenthiuron and (II-1-27) |
| 21e) | (2-17) spinosad and (II-1-27) |
| 21f) | (2-20) endosulfan and (II-1-27) |
| 22a) | (I-1) and (II-1-29) |
| 22b) | (I-2) and (II-1-29) |
| 22c) | (2-2) abamectin and (II-1-29) |
| 22d) | (2-5) diafenthiuron and (II-1-29) |
| 22e) | (2-17) spinosad and (II-1-29) |
| 22f) | (2-20) endosulfan and (II-1-29) |
| 23a) | (I-1) and (II-1-30) |
| 23b) | (I-2) and (II-1-30) |
| 23c) | (2-2) abamectin and (II-1-30) |
| 23d) | (2-5) diafenthiuron and (II-1-30) |
| 23e) | (2-17) spinosad and (II-1-30) |
| 23f) | (2-20) endosulfan and (II-1-30) |
| 24a) | (I-1) and (II-1-31) |
| 24b) | (I-2) and (II-1-31) |
| 24c) | (2-2) abamectin and (II-1-31) |
| 24d) | (2-5) diafenthiuron and (II-1-31) |
| 24e) | (2-17) spinosad and (II-1-31) |
| 24f) | (2-20) endosulfan and (II-1-31) |
| 25a) | (I-1) and (II-1-32) |
| 25b) | (I-2) and (II-1-32) |
| 25c) | (2-2) abamectin and (II-1-32) |
| 25d) | (2-5) diafenthiuron and (II-1-32) |
| 25e) | (2-17) spinosad and (II-1-32) |
| 2Sf) | (2-20) endosulfan and (II-1-32) |
| 26a) | (I-1) and (II-1-33) |
| 26b) | (I-2) and (II-1-33) |
| 26c) | (2-2) abamectin and (II-1-33) |
| 26d) | (2-5) diafenthiuron and (II-1-33) |
| 26e) | (2-17) spinosad and (II-1-33) |
| 26f) | (2-20) endosulfan and (II-1-33) |
| 27a) | (I-1) and (II-1-38) |
| 27b) | (I-2) and (II-1-38) |
| 27c) | (2-2) abamectin and (II-1-38) |
| 27d) | (2-5) diafenthiuron and (II-1-38) |
| 27e) | (2-17) spinosad and (II-1-38) |
| 27f) | (2-20) endosulfan and (II-1-38) |
| 28a) | (I-1) and (II-1-39) |
| 28b) | (I-2) and (II-1-39) |
| 28c) | (2-2) abamectin and (II-1-39) |
| 28d) | (2-5) diafenthiuron and (II-1-39) |
| 28e) | (2-17) spinosad and (II-1-39) |
| 28f) | (2-20) endosulfan and (II-1-39) |
| 29a) | (I-1) and (II-1-40) |
| 29b) | (I-2) and (II-1-40) |
| 29c) | (2-2)abamectin and (II-1-40) |
| 29d) | (2-5) diafenthiuron and (II-1-40) |
| 29e) | (2-17) spinosad and (II-1-40) |
| 29f) | (2-20) endosulfan and (II-1-40) |
| 30a) | (I-1) and (II-1-42) |
| 30b) | (I-2) and (II-1-42) |
| 30c) | (2-2) abamectin and (II-1-42) |
| 30d) | (2-5) diafenthiuron and (II-1-42) |
| 30e) | (2-17) spinosad and (II-1-42) |
| 30f) | (2-20) endosulfan and (II-1-42) |
| 31a) | (I-1) and (II-1-43) |
| 31b) | (I-2) and (II-1-43) |

| No. | Active compound combination comprising |
|---|---|
| 31c) | (2-2) abamectin and (II-1-43) |
| 31d) | (2-5) diafenthiuron and (II-1-43) |
| 31e) | (2-17) spinosad and (II-1-43) |
| 31f) | (2-20) endosulfan and (II-1-43) |
| 32a) | (I-1) and (II-1-44) |
| 32b) | (I-2) and (II-1-44) |
| 32c) | (2-2) abamectin and (II-1-44) |
| 32d) | (2-5) diafenthiuron and (II-1-44) |
| 32e) | (2-17) spinosad and (II-1-44) |
| 32f) | (2-20) endosulfan and (II-1-44) |
| 33a) | (I-1) and (II-1-50) |
| 33b) | (I-2) and (II-1-50) |
| 33c) | (2-2) abamectin and (II-1-50) |
| 33d) | (2-5) diafenthiuron and (II-1-50) |
| 33e) | (2-17) spinosad and (II-1-50) |
| 33f) | (2-20) endosulfan and (II-1-50) |
| 34a) | (I-1) and (II-1-51) |
| 34b) | (I-2) and (II-1-51) |
| 34c) | (2-2) abamectin and (II-1-51) |
| 34d) | (2-5) diafenthiuron and (II-1-51) |
| 34e) | (2-17) spinosad and (II-1-51) |
| 34f) | (2-20) endosulfan and (II-1-51) |
| 35a) | (I-1) and (II-1-52) |
| 35b) | (I-2) and (II-1-52) |
| 35c) | (2-2) abamectin and (II-1-52) |
| 35d) | (2-5) diafenthiuron and (II-1-52) |
| 35e) | (2-17) spinosad and (II-1-52) |
| 35f) | (2-20) endosulfan and (II-1-52) |
| 36a) | (I-1) and (II-1-53) |
| 36b) | (I-2) and (II-1-53) |
| 36c) | (2-2) abamectin and (II-1-53) |
| 36d) | (2-5) diafenthiuron and (II-1-53) |
| 36e) | (2-17) spinosad and (II-1-53) |
| 36f) | (2-20) endosulfan and (II-1-53) |
| 37a) | (I-1) and (II-1-54) |
| 37b) | (I-2) and (II-1-54) |
| 37c) | (2-2) abamectin and (II-1-54) |
| 37d) | (2-5) diafenthiuron and (II-1-54) |
| 37e) | (2-17) spinosad and (I-1-54) |
| 37f) | (2-20) endosulfan and (II-1-54) |
| 38a) | (I-1) and (II-1-55) |
| 38b) | (I-2) and (II-1-55) |
| 38c) | (2-2) abamectin and (II-1-55) |
| 38d) | (2-5) diafenthiuron and (II-1-55) |
| 38e) | (2-17) spinosad and (II-1-55) |
| 38f) | (2-20) endosulfan and (II-1-55) |
| 39a) | (I-1) and (II-1-56) |
| 39b) | (I-2) and (II-1-56) |
| 39c) | (2-2) abamectin and (II-1-56) |
| 39d) | (2-5) diafenthiuron and (II-1-56) |
| 39e) | (2-17) spinosad and (II-1-56) |
| 39f) | (2-20) endosulfan and (II-1-56) |
| 40a) | (I-1) and (II-1-57) |
| 40b) | (I-2) and (II-1-57) |
| 40c) | (2-2) abamectin and (II-1-57) |
| 40d) | (2-5) diafenthiuron and (II-1-57) |
| 40e) | (2-17) spinosad and (II-1-57) |
| 40f) | (2-20) endosulfan and (II-1-57) |
| 41a) | (I-1) and (II-1-58) |
| 41b) | (I-2) and (II-1-58) |
| 41c) | (2-2) abamectin and (II-1-58) |
| 41d) | (2-5) diafenthiuron and (II-1-58) |
| 41e) | (2-17) spinosad and (II-1-58) |
| 41f) | (2-20) endosulfan and (II-1-58) |
| 42a) | (I-1) and (II-1-60) |
| 42b) | (I-2) and (II-1-60) |
| 42c) | (2-2) abamectin and (II-1-60) |
| 42d) | (2-5) diafenthiuron and (II-1-60) |
| 42e) | (2-17) spinosad and (II-1-60) |
| 42f) | (2-20) endosulfan and (II-1-60) |
| 43a) | (I-1) and (II-1-61) |
| 43b) | (I-2) and (II-1-61) |
| 43c) | (2-2) abamectin and (II-1-61) |
| 43d) | (2-5) diafenthiuron and (II-1-61) |
| 43e) | (2-17) spinosad and (II-1-61) |
| 43f) | (2-20) endosulfan and (II-1-61) |
| 44a) | (I-1) and (II-1-62) |
| 44b) | (I-2) and (II-1-62) |
| 44c) | (2-2) abamectin and (II-1-62) |
| 44d) | (2-5) diafenthiuron and (II-1-62) |
| 44e) | (2-17) spinosad and (II-1-62) |
| 44f) | (2-20) endosulfan and (II-1-62) |
| 45a) | (I-1) and (II-1-64) |
| 45b) | (I-2) and (II-1-64) |
| 45c) | (2-2) abamectin and (II-1-64) |
| 45d) | (2-5) diafenthiuron and (II-1-64) |
| 45e) | (2-17) spinosad and (II-1-64) |
| 45f) | (2-20) endosulfan and (II-1-64) |
| 46a) | (I-1) and (II-1-65) |
| 46b) | (I-2) and (II-1-65) |
| 46c) | (2-2) abamectin and (II-1-65) |
| 46d) | (2-5) diafenthiuron and (II-1-65) |
| 46e) | (2-17) spinosad and (II-1-65) |
| 46f) | (2-20) endosulfan and (II-1-65) |
| 47a) | (I-1) and (II-1-66) |
| 47b) | (I-2) and (II-1-66) |
| 47c) | (2-2) abamectin and (II-1-66) |
| 47d) | (2-5) diafenthiuron and (II-1-66) |
| 47e) | (2-17) spinosad and (II-1-66) |
| 47f) | (2-20) endosulfan and (II-1-66) |
| 48a) | (I-1) and (II-1-67) |
| 48b) | (I-2) and (II-1-67) |
| 45c) | (2-2) abamectin and (II-1-67) |
| 48d) | (2-5) diafenthiuron and (II-1-67) |
| 48e) | (2-17) spinosad and (II-1-67) |
| 48f) | (2-20) endosulfan and (II-1-67) |
| 49a) | (I-1) and (II-1-68) |
| 49b) | (I-2) and (II-1-68) |
| 49c) | (2-2) abamectin and (II-1-68) |
| 49d) | (2-5) diafenthiuron and (II-1-68) |
| 49e) | (2-17) spinosad and (II-1-68) |
| 49f) | (2-20) endosulfan and (II-1-68) |
| 50a) | (I-1) and (II-1-69) |
| 50b) | (I-2) and (II-1-69) |
| 50c) | (2-2) abamectin and (II-1-69) |
| 50d) | (2-5) diafenthiuron and (II-1-69) |
| 50e) | (2-17) spinosad and (II-1-69) |
| 50f) | (2-20) endosulfan and (II-1-69) |
| 51a) | (I-1) and (II-1-70) |
| 51b) | (I-2) and (II-1-70) |
| 51c) | (2-2) abamectin and (II-1-70) |
| 51d) | (2-5) diafenthiuron and (II-1-70) |
| 51e) | (2-17) spinosad and (II-1-70) |
| 51f) | (2-20) endosulfan and (II-1-70) |
| 52a) | (I-1) and (II-1-71) |
| 52b) | (I-2) and (II-1-71) |
| 52c) | (2-2) abamectin and (II-1-71) |
| 52d) | (2-5) diafenthiuron and (II-1-71) |
| 52e) | (2-17) spinosad and (II-1-71) |
| 52f) | (2-20) endosulfan and (II-1-71) |
| 53a) | (I-1) and (II-1-72) |
| 53b) | (I-2) and (II-1-72) |
| 53c) | (2-2) abamectin and, (II-1-72) |
| 53d) | (2-5) diafenthiuron and (II-1-72) |
| 53e) | (2-17) spinosad and (II-1-72) |
| 53f) | (2-20) endosulfan and (II-1-72) |

However, the general or preferred radical definitions or illustrations listed above can also be combined with one another as desired, i.e. between their respective ranges and preferred ranges. The definitions apply to the end products and, correspondingly, to precursors and intermediates.

Preference according to the invention is given to active compound combinations comprising compounds of the formula (I) or a compound of group 2 and at least one compound of the formula (II), where the individual radicals are a combination of the meanings listed above as being preferred (preferable).

Particular preference according to the invention is given to active compound combinations comprising compounds of the formula (I) or a compound of group 2 and at least one compound of the formula (II), where the individual radicals are a combination of the meanings listed above as being particularly preferred.

Very particular preference according to the invention is given to active compound combinations comprising compounds of the formula (I) or a compound of group 2 and at least one compound of the formula (II), where the individual radicals are a combination of the meanings listed above as being very particularly preferred.

Saturated or unsaturated hydrocarbon radicals, such as alkyl or alkenyl, can in each case be straight-chain or branched as far as this is possible, including in combination with heteroatoms, such as, for example, in alkoxy.

Optionally substituted radicals can be mono- or polysubstituted, where in the case of polysubstitution the substituents can be identical or different.

In addition, the active compound combinations may also comprise further fungicidally, acaricidally or insecticidally active additives.

If the active compounds in the active compound combinations according to the invention are present in certain weight ratios, the synergistic effect is particularly pronounced. However, the weight ratios of the active compounds in the active compound combinations can be varied within a relatively wide range. In general, the combinations according to the invention comprise active compounds of the formula (I) or a compound of group 2 and the mixing partner of the formula (I) in the preferred and particularly preferred mixing ratios given:

The preferred mixing ratio is from 500:1 to 1:50.

The particularly preferred mixing ratio is from 25:1 to 1:10.

The mixing ratios are based on weight ratios. The ratio is to be understood as meaning active compound of the formula (I):mixing partner of the formula (II) or as ratio of a compound of group 2:mixing partner of the formula (II).

The active compound combinations according to the invention are suitable for controlling animal pests, preferably arthropods and nematodes, in particular insects and arachnids, found in agriculture, in animal health, in forests, in the protection of stored products and materials and in the hygiene sector. They are active against normally sensitive and resistant species, and against all or individual developmental stages. The abovementioned pests include:

From the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus, Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp., *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella occidentalis.*

From the order of the Heteroptera, for example, *Eurygaster* spp., *Dysdercus intermedius, Piesma quadrata, Cimex lectularius, Rhodnius prolixus, Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psyliiodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus.*

From the order of the Hymenoptera, for example, *Diprion* spp., *Hoplocampa* spp., *Lasius* spp., *Monomorium pharaonis, Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of the Siphonaptera, for example, *Xenopsylla cheopis, Ceratophyllus* spp.

From the class of the Arachnida, for example, *Scorpio maurus, Latrodectus mactans, Acarus siro, Argas* spp., *Omithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp.,

*Bryobia praetiosa, Panonychus* spp., *Tetranychus* spp., *Hemitarsonemus* spp., *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus spp.*

The active compound combinations can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, or else water.

Suitable solid carriers are:

for example ammonium salts and ground natural minerals such as kaolins, clays, talc, chalk, quartz, attapulgite, montmorillonite or diatomaceous earth, and ground synthetic materials such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, corn cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compound combinations according to the invention can be present in their commercially available formulations and in the use forms, prepared from these formulations, as a mixture with other active compounds, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Mixtures with other known active compounds such as herbicides or with fertilizers and growth regulators are also possible.

When used as insecticides, the active compound combinations according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and stored-product pests, the active compound combinations are distinguished by an excellent residual action on wood and clay as well as good stability to alkali on limed substrates.

The active compound combinations according to the invention are not only active against plant pests, hygiene pests and stored-product pests, but also, in the veterinary medicine sector, against animal parasites (ectoparasites) such as hard ticks, soft ticks, mange mites, harvest mites, flies (stinging and licking), parasitizing fly larvae, lice, head lice, bird lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp., *Felicola* spp.

From the order *Diptera* and the suborders *Nematocerina* and *Brachycerina*, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattella germanica, Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp.,

*Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compound combinations according to the invention are also suitable for controlling arthropods which attack agricultural livestock such as, for example, cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals such as, for example, hamsters, guinea pigs, rats and mice. By controlling these arthropods, cases of death and reductions in productivity (for meat, milk, wool, hides, eggs, honey and the like) should be diminished, so that more economical and simpler animal husbandry is possible by the use of the active compound combinations according to the invention.

The active compound combinations according to the invention are used in the veterinary sector in a known manner by enteral administration in the form of, for example, tablets, capsules, potions, drenches, granules, pastes, boluses, the feed-through method, suppositories, by parenteral administration such as, for example, by injections (intramuscularly, subcutaneously, intravenously, intraperitoneally and the like), implants, by nasal administration, by dermal administration in the form of, for example, immersing or dipping, spraying, pouring-on, spotting-on, washing, dusting, and with the aid of active-compound-comprising moulded articles such as collars, ear tags, tail tags, limb bands, halters, marking devices and the like.

When used for cattle, poultry, domestic animals and the like, the active compound combinations can be applied as formulations (for example powders, emulsions, flowables) comprising the active compounds in an amount of 1 to 80% by weight, either directly or after 100- to 10 000-fold dilution, or they may be used as a chemical dip.

Moreover, it has been found that the active compound combinations according to the invention show a potent insecticidal action against insects which destroy industrial materials.

The following insects may be mentioned by way of example and with preference, but not by way of limitation:

Beetles such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Dermapterans such as *Sirex juvencus, Urocerus gigas, Urocerus gigas taignus, Urocerus augur*. Termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristle-tails such as *Lepisma saccharina.*

Industrial materials in the present context are understood as meaning non-living materials such as, preferably, polymers, adhesives, glues, paper and board, leather, wood, timber products and paints.

The material which is to be protected from insect attack is very particularly preferably wood and timber products.

Wood and timber products which can be protected by the composition according to the invention, or mixtures comprising it, are to be understood as meaning, for example:

Construction timber, wooden beams, railway sleepers, bridge components, jetties, vehicles made of wood, boxes, pallets, containers, telephone poles, wood lagging, windows and doors made of wood, plywood, chipboard, joinery, or timber products which quite generally are used in house construction or building joinery.

The active compound combinations can be used as such, in the form of concentrates or generally customary formulations such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellant, if desired desiccants and UW stabilizers, and if desired colorants and pigments and other processing auxiliaries.

The insecticidal compositions or concentrates used for protecting wood and timber products comprise the active compound according to the invention in a concentration of 0.0001 to 95% by weight, in particular 0.001 to 60% by weight.

The amount of composition or concentrate employed depends on the species and the abundance of the insects and on the medium. The optimal quantity to be employed can be determined in each case by test series upon application. In general, however, it will suffice to employ 0.0001 to 20% by weight, preferably 0.001 to 10% by weight, of the active compound, based on the material to be protected.

A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wetter.

Organochemical solvents which are preferably employed are oily or oil-type solvents with an evaporation number of above 35 and a flash point of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkylbenzene.

Mineral oils with a boiling range of 170 to 220° C., white spirit with a boiling range of 170 to 220° C., spindle oil with a boiling range of 250 to 350° C., petroleum and aromatics with a boiling range of 160 to 280° C., oil of turpentine, and the like are advantageously used.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility and with an evaporation number of above 35 and a flash point of above 30° C., preferably above 45° C., can be replaced in part by organochemical solvents of high or medium volatility, with the proviso that the solvent mixture also has an evaporation number of above 35 and a flash point of above 30° C., preferably above 45° C., and that the mixture is soluble or emulsifiable in this solvent mixture.

In a preferred embodiment, some of the organochemical solvent or solvent mixture or an aliphatic polar organochemical solvent or solvent mixture is replaced. Aliphatic organochemical solvents which contain hydroxyl and/or ester and/or ether groups are preferably used, such as, for example, glycol ethers, esters or the like.

Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution. Bitumen or bituminous substances may also be used as binders, in amounts of up to 10% by weight. In addition, colorants, pigments, water repellants, odor-masking agents, and inhibitors or anticorrosive agents and the like, all of which are known per se, can be employed.

In accordance with the invention, the composition or the concentrate preferably comprises, as organochemical binders, at least one alkyd resin or modified alkyd resin and/or a drying vegetable oil. Alkyd resins which are preferably used in accordance with the invention are those with an oil content of over 45% by weight, preferably 50 to 68% by weight.

Some or all of the abovementioned binder can be replaced by a fixative (mixture) or plasticizer (mixture). These additives are intended to prevent volatilization of the active compounds, and also crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters such as tributyl phosphate, adipic esters such as di(2-ethylhexyl) adipate, stearates such as butyl stearate or amyl stearate, oleates such as butyl oleate, glycerol ethers or higher-molecular-weight glycol ethers, glycerol esters and p-toluenesulfonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, water, if appropriate as a mixture with one or more of the abovementioned organochemical solvents or diluents, emulsifiers and dispersants.

Particularly effective timber protection is achieved by industrial-scale impregnating processes, for example the vacuum, double-vacuum or pressure processes.

The active compound combinations according to the invention can equally be employed for protecting objects which come into contact with saltwater or brackish water, in particular hulls, screens, nets, buildings, quaysides and signaling systems, against fouling.

Fouling by sessile *Oligochaeta*, such as *Serpulidae*, and by shells and species from the *Ledamorpha* group (goose barnacles), such as various *Lepas* and *Scalpellum* species, or by species from the *Balanomorpha* group (acorn barnacles), such as *Balanus* or *Pollicipes* species, increases the frictional drag of ships and, as a consequence, leads to a marked increase in operation costs owing to higher energy consumption and additionally frequent stops in the dry dock.

Apart from fouling by algae, for example *Ectocarpus* sp. and *Ceramium* sp., in particular fouling by sessile *Entomostraka* groups, which come under the generic term Cirripedia (cirriped crustaceans), is of particular importance.

Surprisingly, it has now been found that the active compound combinations according to the invention have an outstanding antifouling action.

Use of the active compound combinations according to the invention allows the use of heavy metals such as, for example, in bis(trialkyltin) sulfides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulfide, antimony oxide, polymeric butyl titanate, phenyl (bispyridine)bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylenebisthiocarbamate, zinc oxide, copper(I) ethylenebisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferable suitable components in combinations for the antifouling compositions according to the invention are:

algicides such as 2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as benzo[b]thiophenecarboxylic acid cyclohexylamide S,S-dioxide, dichlofluanid, fluorfolpet, 3-iodo-2-propynyl butylcarbamate, tolylfluanid and azoles such as azaconazole, cyproconazole, epoxyconazole, hexaconazole, metconazole, propiconazole and tebuconazole; molluscicides such as fentin acetate, metaldehyde, methiocarb, niclosamid, thiodicarb and trimethacarb;

or conventional antifouling active compounds such as 4,5-dichloro-2-octyl-4-isothiazolin-3-one, diiodomethylparatryl sulfone, 2-(N,N-dimethylthiocarbamoylthio)-5-nitrothiazyl, potassium salts, copper salts, sodium salts and zinc salts of 2-pyridinethiol 1-oxide, pyridine-triphenylborane, tetrabutyldistannoxane, 2,3,5,6-tetrachloro-4-(methylsulfonyl)pyridine, 2,4,5,6-tetrachloro-isophthalonitrile, tetramethylthiuram disulfide and 2,4,6-trichlorophenylmaleimide.

The antifouling compositions used comprise the active compound combinations according to the invention in a concentration of 0.001 to 50% by weight, in particular 0.01 to 20% by weight.

Moreover, the antifouling compositions according to the invention comprise the customary components such as, for example, those described in Ungerer, *Chem. Ind.* 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumen, asphalt and epoxy compounds, small amounts of chlorine rubber, chlorinated polypropylene and vinyl resins.

If appropriate, paints also comprise inorganic pigments, organic pigments or colorants which are preferably insoluble in seawater. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compound combinations are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodnius prolixus, Triatoma infestans*.

They are used as aerosols, pressureless spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment according to the invention of the plants and parts of plants with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetic Modified Organisms), and parts thereof are treated. The terms "parts", "parts of plants" and "plant parts" have been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferred and to be treated according to the invention include all plants which, in the genetic modification, received genetic material which imparts particularly advantageous useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), corn, soya beans, potatoes, cotton, tobacco, oilseed rape and also fruit plants (with the fruits apples, pears, citrus fruits and grapes), and particular emphasis is given to corn, soya beans, potatoes, cotton, tobacco and oilseed rape. Traits that are particularly emphasized are the increased defense of the plants against insects, arachnids, nematodes and slugs and snails by toxins formed in the plants, in particular those formed by the genetic material from Bacillus Thuringiensis (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defense of plants to fungi, bacteria and viruses by Systemic Acquired Resistance (SAR), systemin, phytoalexins, elicitors, as well as resistance genes and correspondingly expressed proteins and toxins. Traits that are furthermore particularly emphasized are the increased tolerance of the plants to certain herbicidally active compounds, for example imidazolinones, sulfonylureas, glyphosate or phosphinotricin (for example the "PAT" gene). The genes in question which impart the desired traits can also be present in combination with one another in the transgenic plants. Examples of "Bt plants" which may be mentioned are corn varieties, cotton varieties, soya bean varieties and potato varieties which are sold under the trade names YIELD GARD® (for example corn, cotton, soya beans), KnockOut® (for example corn), StarLink® (for example corn), Bollgard® (cotton), Nucotn® (cotton) and NewLeaf® (potato). Examples of herbicide-tolerant plants which may be mentioned are corn varieties, cotton varieties and soya bean varieties which are sold under the trade names Roundup Ready® (tolerance to glyphosate, for example corn, cotton, soya bean), Liberty Link® (tolerance to phosphinotricin, for example oilseed rape), IMI® (tolerance to imidazolinones) and STS® (tolerance to sulfonylureas, for example corn). Herbicide-resistant plants (plants bred in a conventional manner for herbicide tolerance) which may be mentioned include the varieties sold under the name Clearfield® (for example corn). Of course, these statements also apply to plant cultivars having these or still-to-be-developed genetic traits, which plants will be developed and/or marketed in the future.

The plants listed can be treated according to the invention in a particularly advantageous manner with the active compound mixtures according to the invention. The preferred ranges stated above for the mixtures also apply to the treatment of these plants. Particular emphasis is given to the treatment of plants with the mixtures specifically mentioned in the present text.

The good insecticidal and acaricidal action of the active compound combinations according to the invention can be seen from the examples which follow. While the individual active compounds show weaknesses in their action, the combinations show an action which exceeds a simple sum of actions.

A synergistic effect in insecticides and acaricides is always present when the action of the active compound combinations exceeds the total of the actions of the active compounds when applied individually.

The expected action for a given combination of two active compounds can be calculated as follows, according to S. R. Colby, Weeds 15 (1967), 20-22:

If

X is the kill rate, expressed as a percentage of the untreated control, when employing active compound A at an application rate of $\underline{m}$ g/ha or in a concentration of $\underline{m}$ ppm, Y is the kill rate, expressed as a percentage of the untreated control, when employing active compound B at an application rate of $\underline{n}$ g/ha or in a concentration of $\underline{n}$ ppm and E is the kill rate, expressed as a percentage of the untreated control, when employing active compounds A and B at application rates of $\underline{m}$ and $\underline{n}$ g/ha or in a concentration of $\underline{m}$ and $\underline{n}$ ppm, then $$E = X + Y - \frac{X \cdot Y}{100}$$

If the actual insecticidal kill rate exceeds the calculated value, the action of the combination is superadditive, i.e. a synergistic effect is present. In this case, the actually observed kill rate must exceed the value calculated using the above formula for the expected kill rate (E).

After the desired period of time, the kill in % is determined. 100% means that all animals have been killed; 0% means that none of the animals have been killed.

USE EXAMPLES

Example A

*Aphis gossypii* Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amount of solvent and emulsifier, and the concentrate is diluted with emulsifier-containing water to the desired concentration.

Cotton leaves (*Gossypium hirsutum*) which are heavily infested by the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed. The kill rates determined are calculated using Colby's formula (see page 44).

In this test, the following active compound combination in accordance with the present application showed a synergistically enhanced activity compared to the active compounds applied on their own:

Example B

*Heliothis armigera* Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the cotton boll worm (*Heliothis armigeia*) while the leaves are still moist.

After the desired period of time, the kill in % is determined. 100% means that all caterpillars have been killed; 0% means that none of the caterpillars have been killed. The kill rates determined are calculated using Colby's formula (see page 44).

In this test, the following active compound combination in accordance with the present application showed a synergistically enhanced activity compared to the active compounds applied on their own:

TABLE A

Plant-damaging insects
*Aphis gossypii* test

| Active compounds | Concentration of active compound in ppm | Kill rate in % after $1^d$ found* | calc.** |
|---|---|---|---|
| 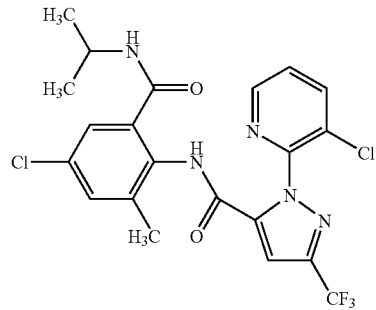 (II-1-9) | 4 | 10 | |
| 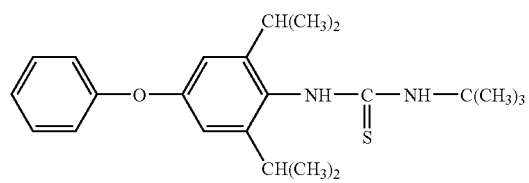 (2-5) diafenthiuron | 20 | 15 | |
| (II-1-9) + (2-5) diafenthiuron (1:5) | 4 + 20 | 55 | 23.5 |

*found = activity found
**calc. = activity calculated using Colby's formula

TABLE B 1

Plant-damaging insects
*Heliothis armigera* test

| Active compounds | Concentration of active compound in ppm | Kill rate in % after 6$^d$ | |
|---|---|---|---|
| | | found* | calc.** |
| (II-1-9) 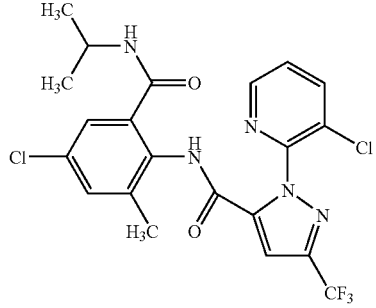 | 0.0064 | 30 | |
| (2-2) abamectin | 0.16 | 50 | |
| (II-1-9) + (2-2) abamectin (1:25) | 0.0064 + 0.16 | 90 | 65 |

*found = activity found
**calc. = activity calculated using Colby's formula

TABLE B 2

Plant-damaging insects
*Heliothis armigera* test

| Active compounds | Concentration of active compound in ppm | Kill rate in % after 3$^d$ | |
|---|---|---|---|
| | | found* | calc.** |
| (II-1-9) | 0.0064 | 10 | |
| (2-17) spinosad | 0.032 | 0 | |

TABLE B 2-continued

Plant-damaging insects
*Heliothis armigera* test

| Active compounds | Concentration of active compound in ppm | Kill rate in % after $3^d$ | |
|---|---|---|---|
| | | found* | calc.** |
| (II-1-9) + (2-17) spinosad (1:5) | 0.0064 + 0.032 | 35 | 10 |

*found = activity found
**calc. = activity calculated using Colby's formula

Example C

*Myzus persicae* Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by being dipped into the preparation of active compound of the desired concentration.

After the desired period of time, the kill in % is determined. 100% means that all aphids have been killed; 0% means that none of the aphids have been killed. The kill rates determined are calculated using Colby's formula (see page 44).

In this test, for example, the following active compound combination in accordance with the present application shows a synergistically enhanced activity compared to the active compounds applied on their own:

TABLE C

Plant-damaging insects
*Myzus persicae* test

| Active compounds | Concentration of active compound in ppm | Kill rate in % after $6^d$ | |
|---|---|---|---|
| | | found* | calc.** |
| (II-1-9) | 4 | 25 | |
| (2-20) endosulfan | 20 | 15 | |
| (II-1-9) + (2-20) endosulfan (1:5) | 4 + 20 | 70 | 36.25 |

*found = activity found
**calc. = activity calculated using Colby's formula

Example D

*Phaedon cochleariae* Larvae Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed. The kill rates determined are calculated using Colby's formula (see page 44).

In this test, the following active compound combination in accordance with the present application showed a synergistically enhanced activity compared to the active compounds applied on their own:

TABLE D 1

| | Plant-damaging insects | | |
| | *Phaedon cochleariae* larvae test | | |
|---|---|---|---|
| Active compounds | Concentration of active compound in ppm | Kill rate in % after $4^d$ found* | calc.** |
| 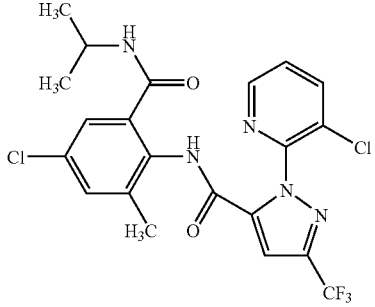 (II-1-9) | 0.16 | 0 | |
| 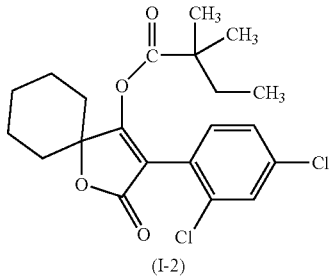 (I-2) | 100 | 0 | |
| (II-1-9) + (I-2) (1:625) | 0.16 + 100 | 30 | 0 |

*found = activity found
**calc. = activity calculated using Colby's formula

TABLE D 2

Plant-damaging insects
Phaedon cochleariae larvae test

| Active compounds | Concentration of active compound in ppm | Kill rate in % after 4$^d$ | |
|---|---|---|---|
| | | found* | calc.** |
| 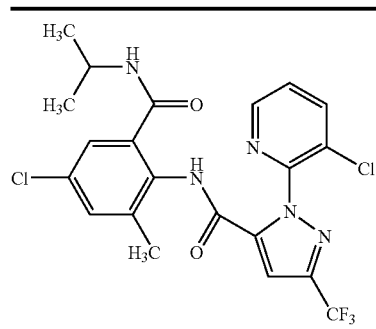<br>(II-1-9) | 0.16 | 5 | |
| 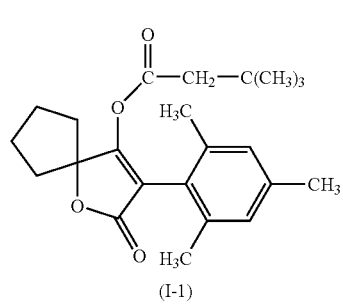<br>(I-1) | 100 | 45 | |
| (II-1-9) + (I-1) (1:625) | 0.16 + 100 | 85 | 47.75 |

*found = activity found
**calc. = activity calculated using Colby's formula

Example E

*Tetranychus urticae* Test (OP-Resistant; Dip Application)

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Bush beans (*Phaseolus vulgaris*) which are heavily infested by the greenhouse red spider mite (*Tetranychus urticae*) are dipped into a preparation of active compound of the desired concentration.

After the desired period of time, the kill in % is determined. 100% means that all spider mites have been killed; 0% means that none of the spider mites have been killed. The kill rates determined are calculated using Colby's formula (see page 44).

In this test, the following active compound combination in accordance with the present application showed a synergistically enhanced activity compared to the active compounds applied on their own:

TABLE E 1

Plant-damaging mites
*Tetranychus urticae* test (OP-resistant, dip application)

| Active compounds | Concentration of active compound in ppm | Kill rate in % after $7^d$ | |
|---|---|---|---|
| | | found* | calc.** |
| (II-1-9) [isopropylcarbamoyl-chloro-methylphenyl-aminocarbonyl-chloropyridinyl-pyrazole-CF₃ structure] | 100 | 0 | |
| (I-2) [spirocyclohexane furanone with dichlorophenyl and pivalate ester structure] | 0.8 | 0 | |
| (II-1-9) + (I-2) (125:1) | 100 + 0.8 | 20 | 0 |

*found = activity found
**calc. = activity calculated using Colby's formula

TABLE E 2

Plant-damaging mites
*Tetranychus urticae* test (OP-resistant, dip application)

| Active compounds | Concentration of active compound in ppm | Kill rate in % after $7^d$ | |
|---|---|---|---|
| | | found* | calc.** |
| (II-1-9) [isopropylcarbamoyl-chloro-methylphenyl-aminocarbonyl-chloropyridinyl-pyrazole-CF₃ structure] | 100 | 0 | |

TABLE E 2-continued

| | | Kill rate in % after 7$^d$ | |
|---|---|---|---|
| Active compounds | Concentration of active compound in ppm | found* | calc.** |
| 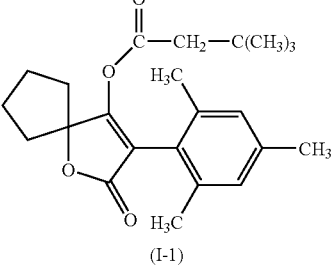 (I-1) | 0.8 | 65 | |
| (II-1-9) + (I-1) (1:625) | 0.16 + 100 | 95 | 65 |

*found = activity found
**calc. = activity calculated using Colby's formula

The invention claimed is:

1. A composition comprising a synergistically effective amount of abamectin and the compound of formula (II-1-4):

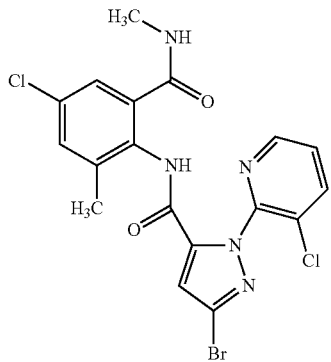

wherein the ratio of said abamectin to the compound of formula (II-1-4) is 25:1 to 1:10.

2. A method of controlling insects or arachnids comprising contacting the composition according to claim 1 with said insects or arachnids.

3. A process for preparing an insecticide, comprising mixing the composition according to claim 1 with extenders and/or surfactants.

* * * * *